(12) United States Patent
Carlson

(10) Patent No.: US 6,369,101 B1
(45) Date of Patent: Apr. 9, 2002

(54) THERAPEUTIC METHOD TO TREAT HERPES VIRUS INFECTION

(75) Inventor: Robert M. Carlson, Duluth, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/259,626

(22) Filed: Feb. 26, 1999

(51) Int. Cl.$^7$ ................... A61K 31/34; C07D 307/77; C07D 307/00

(52) U.S. Cl. ................ 514/468; 514/461; 514/462; 514/449; 549/429; 549/456

(58) Field of Search ............... 549/429, 456; 514/468, 461, 462

(56) References Cited

U.S. PATENT DOCUMENTS

| | | | |
|---|---|---|---|
| 4,732,708 A | 3/1988 | Ekman et al. | 260/413 |
| 5,468,888 A | 11/1995 | Bouboutou et al. | 554/58 |
| 5,529,769 A | 6/1996 | Cho et al. | 424/74 |
| 5,658,947 A | 8/1997 | DasGupta et al. | 514/510 |
| 5,679,828 A | 10/1997 | Lee et al. | 560/116 |
| 5,750,578 A | * 5/1998 | Carlson et al. | 514/766 |
| 5,804,575 A | 9/1998 | Pezzuto et al. | 514/169 |

FOREIGN PATENT DOCUMENTS

| | | |
|---|---|---|
| EP | 0325460 | 7/1989 |
| WO | WO86/01516 | 3/1986 |
| WO | WO94/26695 | 11/1994 |
| WO | WO94/26725 | 11/1994 |
| WO | WO96/39033 | 12/1999 |

OTHER PUBLICATIONS

Platanov et al. (CA 123:33428, abstract of Khim.–Farm. Zh. (1995), 29(2), pp. 42–46), 1995.*

Eugster et al. (CA 129:166219 abstract of WO 9832443), 1998.*

Odinokova et al. (CA 103:51225, abstract of Khim. Prirr. Soedin. (1985), (3), p. 414), 1985.*

Ryu, Shi Yong et al. (DN 118:230194, CAPLUS, abstract of Arch. Pharmacal. Res. (1992), 15(3), 242–5).*

Cordeiro, N., et al., "Cork suberin as a new source of chemicals. 1. Isolation and chemical characterization of its composition", *International Journal of Biological Macromolecules, 22*, pp. 71–80, (1998).

Eckerman, C., et al., "Comparison of Solvents for Extraction and Crystallisation of Betulinol from Birch Bark Waste", *Paperi ja Puu—Papper och Trä, No. 3*, pp. 100, 102–3, & 105–6, (1985).

(List continued on next page.)

*Primary Examiner*—Sabiha Qazi
(74) *Attorney, Agent, or Firm*—Schwegman, Lundberg, Woessner & Kluth, P.A.

(57) ABSTRACT

A therapeutic method is provided for treating a mammal afflicted with a herpesvirus infection, comprising administering an effective amount of a compound of formula I:

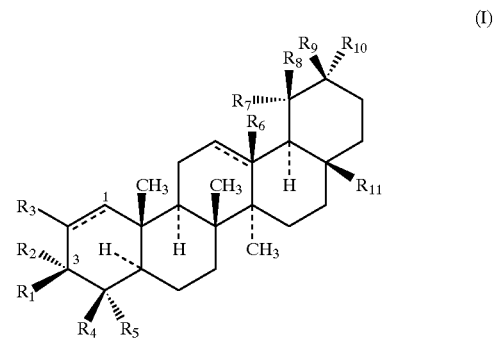

wherein $R_1$–$R_{11}$, have any of the values disclosed in the specification; or a pharmaceutically acceptable salt thereof. The invention also provides novel compounds of formula I, and pharmaceutical compositions comprising compounds of formula I.

44 Claims, 1 Drawing Sheet

OTHER PUBLICATIONS

Ekman, R., "The Suberin Monomers and Triterpenoids from the Outer Bark of Betula verrucosa Ehrh", *Holzforschung, 37*, pp. 205–211, (1983).

Fulda, S., et al., "Betulinic acid triggers CD95 (APO–1/Fas)—and p53–independent apoptosis via activation of caspases in neuroectodermal tumors", *Cancer Research, 57* (21), pp. 4956–4964, (Nov. 1, 1997).

Jääskläinen, P., "Betulinol and its utilisation", *Paperi ja Puu—Papper Och Trära, 63* (10), pp. 599–603, (Oct. 1981).

Kolattukudy, P.E., "Structure, Biosynthesis, and Biodegradation of Cutin and Suberin", *Annual Review of Plant Physiology*, 32, pp. 539–567, (1981).

Laks, P.E., et al., "Flavonoid Biocides: Wood Preservatives Based on Condensed Tannins", *Holzforschung, 42*, pp. 299–306, (1988).

Màñz, S., et al., "Effect of selected triterpenoids on chronic dermal inflammation", *European Journal of Pharmacology, 334* (1), pp. 103–105, (Sep. 3, 1997).

Miles, D.H., et al., "Boll Weevil Antifeedants from Elecharis dulcis Trin.", *Journal of Agricultural and Food Chemistry, 42*, pp. 1561–1562, (1994).

Nowak, G.A., "Cosmetic and medicinal properties of the birch", *American Perfumer and Cosmetics, 81*, pp. 37–39, (Nov. 1966).

O'Connell, M.M., et al., "Betulin and Lupeol in Bark from Four White–Barked Birches", *Phytochemistry, 27* (7), pp. 2175–2176, (1988).

Ohara, S., et al., "Utilization of Wood Extractives I. Extractives from the bark of Betula platyphylla Sukatchev var. japonica Hara", *Mokuzai Gakkaishi, 32* (4), pp. 266–273, (1986).

Pearce, R.B., "Suberin in the sapwood of oak (Quercus robur L.) its composition from a compartmentalization barrier and its occurence in tyloses in undecayed wood", *Physiological Plant Pathology, 24*, 71–81, (1984).

Pizzi, A., "Wood/Bark Extracts as Adhesives and Preservatives", *Forest Products Biotechnology, Chapter 11*, Dr. Alan Bruce, et al., (editor), Taylor & Francis, Ltd., London, pp. 167–182, (1998).

Quéré, L., et al., "Triterpenes a Potential Dimerization Inhibitors of HIV–1 Protease", *Biochemical and Biophysical Research Communications, 227*, pp. 484–488, (1996).

Recio, M.D., et al., "Investigation on the Steroidal Anti–Inflammatory Activity of Triterpenoids from Diospyros leucomelas", *Plant Medica, 61*, pp. 9–12, (Feb. 1995).

Roberts, M.T., et al., "Birch (bark)", Bookbinding and the Conservation of Books—A Dictionary of Descriptive Terminology (Website), http://sul–server–2.standford.edu/don/dt/dt0328.html, 2 p., (Jun. 7, 2000).

Sanz, V., et al., "Synthesis of Ambrettolide from Phloionolic Acid", *Journal of the Chemical Society Perkin Transactions I, (7)*, pp. 1837–1839, (Jul. 1982).

Schmidt, M.L., et al., "Betulinic acid induces apoptosis in human neuroblastoma cell lines", *European Journal of Cancer, 33* (12), pp. 2007–2010, (Oct. 1997).

Schweizer, P., et al., "Induction of resistance in barley against Erysiphe graminis f.sp. hordei by free cutin monomers", *Physiological and Molecular Plant Pathology, 49*, pp. 103–120, (1996).

Seoane, E., et al., "Total Synthesis and Stereochemistry of Phloiononolic Acids", *Anales De Quimica, 73*, pp. 1336–1339, (1977).

Soler, F., et al., "Betulinic acid derivatives: a new class of specific inhibitors of human immunodeficiency virus type 1 entry", *Journal of Medicinal Chemistry, 39* (5), pp. 1069–1083, Mar. 1, 1996).

Wang, J., et al., "Antibechic and expectorant constituents of Huashupi (Betulae cortex)", *Zhongguo Yaoxue Zazhi, 29* (5), pp. 268–271, (1994).

Yasukawa, K., et al., "Sterol and triterpene derivatives from plants inhibit the effects of a tumor promoter, and sitsterol and betulinic acid inhibit tumor formation in mouse skin two–stage carcinogenesis", *Oncology, 48* (1), pp. 72–76, (1991).

Arbesfeld, D.M., et al., "Cutaneous Herpes Simples Virus Infections", American Family Physician, vol. 43, No. 5, 1655–1664, (May 1991).

Baltina, L.A., et al., "The Synthesis of Triterpene 2,6–Dideoxy–alpha–L–arabino–Hexopyranosides from L–Rhamnal and Their Pharmacological Properties", Russian Journal of Bioorganic Chemistry, vol. 23, No. 10, 745–750, (1997).

Bean, B., "Acyclovir in the treatment of herpesvirus infections", HerpesVirus Infections, Postgraduate Medicine, vol. 73, No. 3, 297–303, (Mar. 1983).

Challand, R., et al., "Herpes Viruses", *Antiviral Chemotherapy*, Biochemical & Medicinal Series, Chapeter 6, 54–67, (1997).

Chatis, P.A., et al., "Analysis of the Thymidine Kinase Gene form Clinically Isolated Acyclovir–Resistant Herpes Simplex Viruses", Virology 180, 793–797, (1991).

Haase, A.T., "Methods in Viral Pathogenesis: Tissues and Organs", *Viral Pathogenesis*, Chapter 19, 465–482, (1997).

Hayek, E.W., et al., "A Bicentennial of Betulin", *Phytochemistry*, Review Article No. 46, vol. 28, No. 9, 2229–2242, (1989).

Konoshima, T., et al., "Studies on Inhibitors of Skin Tumor Promotion, III. Inhibitory Effects of Isoflavonoids form Wisteria Brachybotrys on Epstein–Barr Epstein–Barr Virus Activation", Journal of Natural Products, vol. 51, No. 6, 1266–1270, (1988).

Lugemwa, F.N., et al., "A Heliothis zea Angifeedant from the Abundant Birchbark Triterpene Betulin", Journal of Agricultural and Food Chemistry, 493–496, (Feb. 1990).

Odinokova, L.E., et al., Khim.Prir. Soedin discloses specific allobetulin derivatives. See p. 184, 182–187, (1984).

Patra, A., et al., "Studies on Triterpenoids: Treatment of 3–Acetylbetulinic Acid with m–Chloroperbenzoic Acid & Sulphuric Acid", Indian Journal of Chemistry, vol. 27B, 170–172, (Feb. 1988).

Pisha, E., et al., "Discovery of Betulinic Acid as a Selective Inhibitor of Human Melanoma that Functions by Induction of Apoptosis", Nature Medicine, vol. 1, No. 10, 1046–1051, (Oct. 1995).

Roizman, B., et al., "An Inquiry into the Mechanisms of Herpes Simplex Virus Latency", Annual Review of Mircobiology, vol. 41, 544–571, (1987).

Roizman, B., et al., "Herpes Simplex Viruses and Their Replication", *Virology*, Second Edition, Chapter 65, 1795–1841, (1990).

Schmidt, J., et al., "Mass Spectroscopy of Natural Products: V–Mass Spectroscopy Studies of Ring A Substituted Allobetulane Derivatives", Organic Mass Spectrometry, vol. 14, No. 12, 646–655, (1979).

* cited by examiner

Figure I
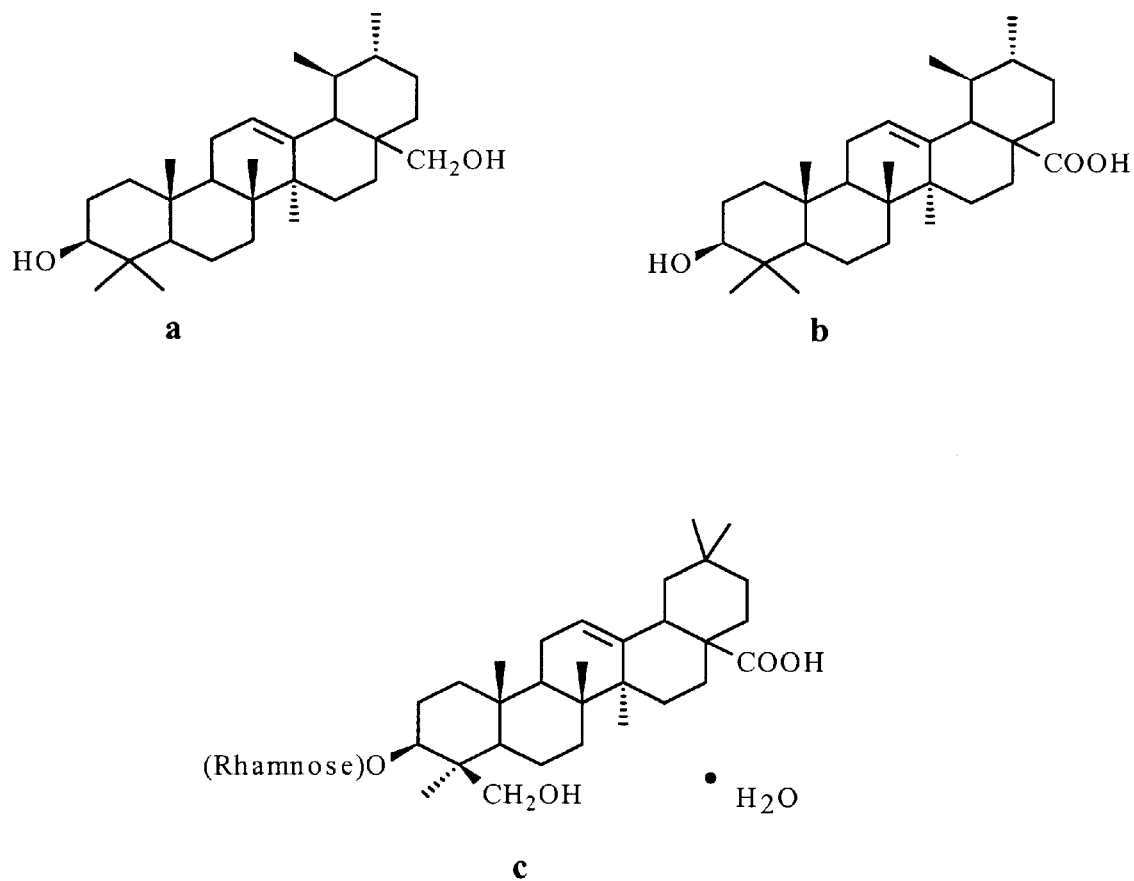

THERAPEUTIC METHOD TO TREAT HERPES VIRUS INFECTION

BACKGROUND OF THE INVENTION

The herpes simplex viruses (HSV) are a group of about 100 different double-stranded DNA animal viruses. At least seven are known to be pathogenic to humans and are known as human herpes viruses or HHV. HHV include herpes simplex virus type 1 and type 2 (HSV-1 and HSV-2), varicella zoster virus (VSV or HHV3, which causes chickenpox), cytomegalovirus (HCMV), human herpesvirus type 6 and type 7 (HHV-6 and HHV-7) and Epstein-Barr virus (EBV or HHV4 which causes infectious mononucleosis). Infections by these viruses are among the most common and easily transmitted viral infections, afflicting greater than one million individuals each year in the United States. The hallmark of herpes virus infections is latency. The site of latency is the dorsal root ganglia or the sacral ganglia. Here the virus remains latent and can be reactivated under various conditions of stress. See, for example, B. Roizman et al., *Am. Rev. Microbiol.*, 41, 543 (1987); B. Roizman et al., "Herpes Simplex and Their Replication", B. Fields, ed., *Virology*, Raven Press, NY (2d ed., 1990) at pp. 1795–1841; A. H. Haase et al., *Viral Pathogenesis*, N. Nathanson, ed., Lippincott-Raven (1996) at pp. 465–506.

HSV-1 mainly affects areas above the waist and is most common in children between the ages of one and five. HSV-2 is primarily a sexually transmitted virus affecting the genital areas, sacrum and buttocks. These two types can infect any mucutaneous surface or visceral site and produce clinically indistinguishable lesions. The degree of infection greatly varies from patient to patient, however, those with T-cell defects experience more frequent and severe HSV infections (D. M. Arbesfeld et al., *Am. Family Physician*, 43, 1655 (1991)).

Numerous treatments for HSV infections have been tried and none have been entirely satisfactory. Chemotherapy (topical or systemic) for HSV infection has included the use of idoxuridine, trifluorothymidine, adenine arabinoside (ara-A), acyclovir, bromovinyl deoxyuridine, foscarnet, and other acyclic nucleoside analogues. Among all the anti-HSV agents, acyclovir (ACV) was the first genuinely selective agent. It profoundly affects viral DNA polymerase function through obligatory chain termination and competitive inhibition. See B. Beam, *Postgrad. Med.*, 77, 297 (1983). The poor absorption rate and pharmacokinetics of acyclovir have been overcome to some extent by the use of prodrugs like valaciclovir and penciclovir in treating infected individuals. However, many HSV-1 and HSV-2 strains have produced mutants that are resistant to ACV. Also, drugs such as ACV require the virus to be actively multiplying and are not active when the virus is latent. The greatest difficulty in finding antiviral compounds is due to the requirement that the active compound must act on virus within a host cell without causing damage to the host cell (A. Chatos et al., *Virol.*, 180, 793 (1991)).

U.S. Pat. No. 5,750,578, issued May 12, 1998, discloses that betulin and certain specific analogs thereof possess antiviral activity. However, there is a continuing need for additional antiviral and antibacterial agents, useful to treat herpes viruses.

SUMMARY OF THE INVENTION

The present invention provides a therapeutic method for treating a human afflicted with herpesvirus infection comprising administering to said human an effective anti-viral amount of a compound of formula (I):

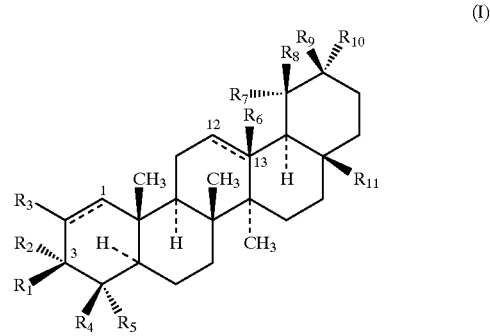

wherein
one of $R_1$ and $R_2$ is —O—Y and the other is hydrogen or $(C_1-C_6)$alkyl optionally substituted by hydroxy, $(C_1-C_6)$alkoxy, halo, halo$(C_1-C_6)$alkoxy or $NR_jR_k$ wherein $R_j$ and $R_k$ are independently H, $(C_1-C_6)$alkyl or $(C_1-C_6)$alkonyl; or $R_1$ and $R_2$ together are oxo (=O);

$R_3$ is hydrogen, halo, carboxy, mercapto, $(C_1-C_6)$alkyl, $(C_3-C_8)$cycloalkyl, or —O—Y;

$R_4$ and $R_5$ are each independently hydrogen, $(C_1-C_6)$alkyl, or hydroxy$(C_1-C_6)$alkyl;

$R_6$ is hydrogen or is absent when the adjacent—is a bond;

$R_7$ is hydrogen or $(C_1-C_6)$alkyl;

$R_8$ is hydrogen, $(C_1-C_6)$alkyl, or hydroxy$(C_1-C_6)$alkyl and $R_{11}$, is hydrogen, $(C_1-C_6)$alkyl, carboxy, or hydroxy$(C_1-C_6)$alkyl; or $R_8$ and $R_{11}$ together are —O—C(=X)—;

$R_9$ and $R_{10}$, are each independently hydrogen or $(C_1-C_6)$alkyl;

each of the bonds represented by—is independently absent or is present;

X is two hydrogens, oxo (=O) or thioxo (=S);

each Y is independently H, aryl, $P(O)(C)_2$, $(C_3-C_8)$cycloalkyl, adamantyl, —$SO_2R_a$ O=P$(R_b)_2$, O=P$(R_c)_2$ OP(O)$(R_d)$—, Si$(R_e)_3$, tetrahydropyran-2-yl, an amino acid, a peptide, a glycoside, or a 1 to 10 membered branched or unbranched carbon chain optionally comprising 1, 2, or 3 heteroatoms selected from non-peroxide oxy, thio, and —N$(R_f)$—; wherein said chain may optionally be substituted on carbon with 1, 2, 3, or 4 oxo (=O), hydroxy, carboxy, halo, mercapto, nitro, —N$(R_g)(R_h)$, $(C_3-C_8)$cycloalkyl, $(C_3-C_8)$cycloalkyloxy, aryl, aryloxy, adamantyl, adamantyloxy, hydroxyamino, trifluoroacetylamino, a glycoside, an amino acid, or a peptide; and wherein said chain may optionally be saturated or unsaturated (e.g. containing one, two, three or more, double or triple bonds);

$R_a$ is $(C_1-C_6)$alkyl or aryl;

$R_b$, $R_c$, and $R_d$ are each independently hydroxy, $(C_1-C_6)$alkoxy, hydroxy$(C_2-C_6)$alkoxy, adamantyloxy, adamantyl$(C_1-C_6)$alkoxy, norbomyloxy, 1,1-di(hydroxymethyl)-2-hydroxyethoxy, carboxy$(C_1-C_6)$alkoxy, 2,3-epoxypropyloxy, benzyloxy, $(C_3-C_8)$cycloalkyloxy, $NR_xR_y$, or aryloxy;

$R_e$ is H, aryl or $(C_1-C_6)$alkyl;

$R_f$ is hydrogen, $(C_1-C_6)$alkyl, $(C_1-C_6)$alkanoyl, phenyl or benzyl;

$R_g$ and $R_h$ are each independently selected from the group consisting of hydrogen, $(C_1-C_6)$alkyl, hydroxy$(C_1-C_6)$alkyl, adamantyl, adamantyl $(C_1-C_6)$alkyl, amino$(C_1-C_6)$alkyl, aminosulfonyl, $(C_1-C_6)$alkanoyl, aryl and benzyl; or $R_b$ and $R_c$ together with the nitrogen to which they are attached form a pyrrolidino, piperidino, or morpholino radical; and $R_x$ and $R_y$ are each independently hydrogen, $(C_1-C_6)$ alkyl, $(C_1-C_6)$alkanoyl, aryl or benzyl;

wherein each aryl of Y, $R_a-R_d$, $R_g-R_h$, $R_x$, and $R_y$ may optionally be substituted by 1, 2, or 3 aminosulfonyl, carboxy, $NR_iR_j$, $(C_1-C_6)$alkyl, $(C_1-C_6)$alkoxy, hydroxy, halo, nitro, cyano, mercapto, carboxy, hydroxy$(C_1-C_6)$alkyl, halo $(C_1-C_6)$alkyl, trifluoromethoxy, $(C_1-C_6)$alkanoyl, $(C_1-C_6)$alkoxycarbonyl, $(C_1-C_6)$alkylthio, or $(C_1-C_6)$alkanoyloxy; wherein $R_i$ and $R_j$ are each independently hydrogen, $(C_1-C_6)$alkyl, $(C_1-C_6)$ alkanoyl, phenyl, or benzyl;

or a pharmaceutically acceptable salt thereof.

The invention also provides novel compounds of formula I, as well as intermediates and processes useful for preparing compounds of formula I. The compound of formula (I): 3β-hydroxy-19αH-19,28-epoxy-oleanane is known as allobetulin. Additionally, the compounds uvaol, ursolic acid, and hederin hydrate are known compounds of formula I (see FIG. I). Accordingly, compounds of the formula I preferably exclude allobetulin, uvaol, ursolic acid, and hederin hydrate. Compounds of the invention also preferably exclude the corresponding acetates of these alcohols.

J. Schmidt and S. Huneck *Organic Mass Spectrometry*, 1979, 14, 646–655 disclose the mass spectrometry behavior of certain compounds of formula (I). Accordingly, compounds of the invention preferably exclude:

a) a compound of formula (I) wherein: $R_1$ is OH; when $R_2$ is hydrogen, $R_3$ is hydrogen, $R_4$ is methyl, $R_5$ is methyl, $R_6$ is hydrogen, $R_7$ is hydrogen, $R_9$ is methyl, $R_{10}$ is methyl, the bond at the 1 and 2 positions represented by --- is present or absent, the bond at the 12 and 13 positions represented by --- is absent, and $R_8$ and $R_{11}$ together are —O–CH$_2$—.

b) a compound of formula (I) wherein: $R_1$ is hydroxy or acetoxy;

when $R_2$ is hydrogen, $R_3$ is hydrogen, $R_4$ is methyl, $R_5$ is methyl, $R_6$ is hydrogen, $R_7$ is hydrogen, $R_9$ is methyl, $R_{10}$ is methyl, the bond at the 1 and 2 positions represented by—is present or absent, the bond at the 12 and 13 positions represented by—is absent, and $R_8$ and $R_{11}$ together are —O—CH$_2$—; and c) a compound of formula (I) wherein: $R_1$ and $R_2$ together are oxo;

when $R_3$ is hydrogen, $R_4$ is methyl, $R_5$ is methyl, $R_6$ is hydrogen, $R_7$ is hydrogen, $R_9$ is methyl, $R_{10}$ is methyl, the bond at the 1 and 2 positions represented by --- is present or absent, the bond at the 12 and 13 positions represented by --- is absent, and $R_8$ and $R_{11}$ together are —O—CH$_2$.

L. E. Odinokova et al. *Khim. Prir. Soedin.*, 1961, 2, 182–187 disclose specific allobetulin derivatives. Accordingly compounds of the invention preferably exclude compounds of formula (I) wherein $R_1$ is —O—Y, Y is:

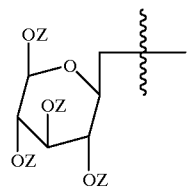

and each Z is hydrogen or acyl; when $R_2$ is hydrogen, $R_3$ is hydrogen, $R_4$ is methyl, $R_5$ is methyl, $R_6$ is hydrogen, $R_7$ is hydrogen, $R_9$ is methyl, $R_{10}$ is methyl, the bond at the 1 and 2 positions represented by --- is absent, the bond at the 12 and 13 positions represented by --- is absent, and $R_8$ and $R_{11}$ together are —O—CH$_2$—.

A. Patra and S. Chaudhuri, *Indian J. Chemistry*, 1988, 27B, 170–172 disclose the conversion of 3-acetylbetulinic acid to 3-acetylbetulinic lactone.

Accordingly, compounds of the invention preferably exclude a compound of formula (I) wherein: $R_1$ is acetoxy; when $R_2$ is hydrogen, $R_3$ is hydrogen, $R_4$ is methyl, $R_5$ is methyl, $R_6$ is hydrogen, $R_7$ is hydrogen, $R_9$ is methyl, $R_{10}$ is methyl, the bond at the 1 and 2 positions represented by --- is absent, the bond at the 12 and 13 positions represented by --- is absent, and $R_8$ and $R_{11}$ together are —O—C (=O)—.

L. A. Baltina et al., *Russian Journal of Bioorganic Chemistry*, 1997, 23, 745–750 disclose the synthesis of certain L-Rhamnal derivatives of formula (I). Accordingly compounds of the invention preferably exclude compounds of formula (I) wherein $R_1$ is:

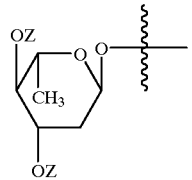

wherein each Z is hydrogen or acetyl; when $R_2$ is hydrogen, $R_3$ is hydrogen, $R_4$ is methyl, $R_5$ is methyl, $R_6$ is hydrogen, $R_7$ is hydrogen, $R_9$ is methyl, $R_{10}$ is methyl, the bond at the 1 and 2 positions represented by --- is absent, the bond at the 12 and 13 positions represented by --- is absent, and $R_8$ and $R_{11}$ together are —O—CH$_2$—.

F. N. Lugemwa et al., *J. Agric. Food Chem.* 1990, 36, 493–496 disclose the preparation and biological screening of certain compounds of formula (I). Accordingly, the compounds of the invention preferably exclude a compound of formula (I) wherein: $R_1$ and $R_2$ together are oxo; when $R_3$ is hydroxy, $R_4$ is methyl, $R_5$ is methyl, $R_6$ is hydrogen, $R_7$ is hydrogen, $R_9$ is methyl, $R_{10}$ is methyl, the bond at the 1 and 2 positions represented by --- is present, the bond at the 12 and 13 positions represented by --- is absent, and $R_8$ and $R_{11}$ together are —O—CH$_2$.

The compounds of the invention also preferably exclude a compound of formula (I) wherein $R_1$ and $R_2$ tog ether are oxo; when $R_3$ is:

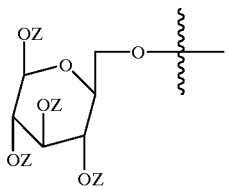

and each Z is hydrogen or acyl; $R_4$ is methyl, $R_5$ is methyl, $R_6$ is hydrogen, $R_7$ is hydrogen, $R_9$ is methyl, $R_{10}$ is methyl, the bond at the 1 and 2 positions represented by --- is present, the bond at the 12 and 13 positions represented by --- is absent, and $R_8$ and $R_{11}$ together are —O—$CH_2$.

The invention also provides a pharmaceutical composition comprising a compound of formula I, or a pharmaceutically acceptable salt thereof, and a pharmaceutically acceptable carrier. Preferably, the pharmaceutical composition of the invention excludes compounds of formula (I) wherein $R_1$ is:

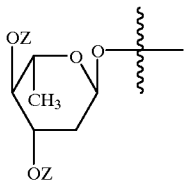

wherein each Z is acetyl; when $R_2$ is hydrogen, $R_3$ is hydrogen, $R_4$ is methyl, $R_5$ is methyl, $R_6$ is hydrogen, $R_7$ is hydrogen, $R_9$ is methyl, $R_{10}$ is methyl, the bond at the 1 and 2 positions represented by --- is absent, the bond at the 12 and 13 positions represented by --- is absent, and $R_8$ and $R_{11}$ together are —O—$CH_2$—.

The pharmaceutical composition of the invention also preferably excludes a compound of formula (I) wherein $R_1$ and $R_2$ together are oxo; when $R_3$ is:

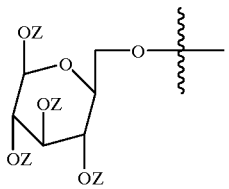

each Z is hydrogen or acyl; $R_4$ is methyl, $R_5$ is methyl, $R_6$ is hydrogen, $R_7$ is hydrogen, $R_9$ is methyl, $R_{10}$ is methyl, the bond at the 1 and 2 positions represented by --- is present, the bond at the 12 and 13 positions represented by --- is absent, and $R_8$ and $R_{11}$ together are —O—$CH_2$.

The pharmaceutical composition of the invention also preferably excludes allobetulin, uvaol, ursolic acid, and hederin hydrate and pharmaceutically acceptable salts thereof; and can also exclude the corresponding acetates of these alcohols.

The invention also provides a compound of formula I for use in medical therapy (preferably for use in treatment of herpesvirus infection), as well as the use of a compound of the invention for the manufacture of a medicament useful for the treatment of herpesvirus infection. Preferably, a compound of formula I for use in medical therapy excludes compounds of formula I that, as disclosed above, can preferably be excluded from the pharmaceutical compositions of the invention.

The compounds of formula (I) may be administered as pharmaceutical compositions, locally or systemically, and are effective to treat (block or inhibit) herpesvirus infections, including active or latent infections. Susceptible herpesvirus infections include HSV-1, HSV-2, VZV, HCMV, HHV-6, HHV-7 or HHV4 (Epstein-Barr virus) infections. Compounds of formula (I) are particularly effective against HSV-1 and HSV-2.

DESCRIPTION OF THE FIGURES

FIG. I shows the structure of uvaol (a), ursolic acid (b), and α-hederin hydrate (c).

DETAILED DESCRIPTION OF THE INVENTION

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. Additionally, alkyl denotes both unsubstituted and substituted hydrocarbon groups. Such substituted groups may contain one or more of the following, halogen, nitro, amino, hydroxy and trifluoromethyl. Aryl denotes a phenyl radical or an ortho-fused bicyclic carbocyclic radical having about nine to ten ring atoms in which at least one ring is aromatic. Additionally, aryl denotes both unsubstituted and substituted cyclic hydrocarbon groups. Such substituted rings may contain one or more of the following, halogen, nitro, amino, hydroxy and trifluoromethyl.

The term "amino acid," comprises the residues of natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). An amino acid can conveniently be linked to a carbon of the remainder of a compound of formula I through the carboxy terminus, the amino terminus, or through any other convenient point of attachment, such as, for example, through the sulfur of cysteine. An amino acid can conveniently be linked to a heteroatom of the remainder of a compound of formula I through the carboxy terminus or through any other convenient point of attachment.

The term "peptide" describes a sequence of 2 to 10 amino acids or peptidyl residues. A peptide can conveniently be linked to a carbon of the remainder of a compound of formula I through the carboxy terminus, the amino terminus, or through any other convenient point of attachment, such as, for example, through the sulfur of cysteine. A peptide can also conveniently be linked to a heteroatom of the remainder of a compound of formula I through the carboxy terminus or through any other convenient point of attachment. Preferably a peptide is a sequence of 2 to 5 amino acids. Peptide derivatives can be prepared as disclosed in U.S. Pat. Nos. 4,612,302; 4,853,371; and 4,684,620.

Glycosides are formed by reacting mono-, di- or polysaccharides, or derivatives thereof with 1 or 2 hydroxyl groups of a compound of formula (I). For example, glycosides can comprise naturally occurring aldoses or hexoses as well as mono-or di-deoxy derivatives thereof. Suitable saccharides include glucose, glucuronic acid, mannose, rhamnose, galactose, sorbase, ribose, maltose, sucrose, modified cellulosics, dextrans, modified starches and the like. Other suitable saccharides are described in the "CRC Handbook of Chemistry and Physics" 64 ed. Robert C. Weast editor, CRC Press, Inc. Boca Raton, Fla. C-725 to C-732. Glycosides can advantageously exhibit improved water solubility over the corresponding alcohol. See, *Remington's Pharmaceutical Sciences*, A. R. Gennaro, ed., Mack Pub. Co. (18th ed., 1990) at pages 384–386. Glycoside derivatives can be prepared as described in PCT Applications WO 96/34005 and 97/03995.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine activity against herpesvirus using the tests described hereinbelow, or using other tests which are well known in the art. Preferred compounds of formula I have the absolute stereochemistry shown in formula I.

Specific values listed below for radicals, substituents, and ranges, are for illustration only; they do not exclude other defined values or other values within defined ranges for the radicals and substituents.

Specifically, $(C_1-C_4)$alkyl can be methyl, ethyl, propyl, isopropyl, butyl, iso-butyl, or sec-butyl; $(C_1-C_6)$alkyl can be methyl, ethyl, propyl, isopropyl, butyl, iso-butyl, sec-butyl, pentyl, 3-pentyl, or hexyl; $(C_3-C_8)$cycloalkyl can be cyclopropyl, cyclobutyl, cyclopentyl, cyclohexyl, cyclohexyl, or cyclooctyl; $(C_1-C_4)$alkoxy can be methoxy, ethoxy, propoxy, isopropoxy, butoxy, iso-butoxy, or sec-butoxy; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_1-C_5)$alkanoyl can be acetyl, propanoyl, butanoyl, or pentanoyl; $(C_1-C_6)$alkanoyl can be acetyl, propanoyl, butanoyl, pentanoyl, or hexanaoyl; halo $(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 2,3-dihydroxypropyl, 1-hydroxybutyl, 4-hydroxybutyl, 2,4-dihydroxybutyl, 1-hydroxypentyl, 5-hydroxypentyl, 1-hydroxyhexyl, or 6-hydroxyhexyl; carboxy$(C_1-C_6)$alkyl can be carboxymethyl, 1-carboxyethyl, 2-carboxyethyl, 1-carboxypropyl, 2-carboxypropyl, 3-carboxypropyl, 2,3-dicarboxypropyl, 1-carboxybutyl, 4-carboxybutyl, 2,4-dicarboxybutyl, 1-carboxypentyl, 5-carboxypentyl, 1-carboxyhexyl, or 6-carboxyhexyl; carboxy$(C_1-C_6)$alkoxy can be carboxymethoxy, 1-carboxyethoxy, 2-carboxyethoxy, 1-carboxypropoxy, 2-carboxypropoxy, 3-carboxypropoxy, 2,3-dicarboxypropoxy, 1-carboxybutoxy, 4-carboxybutoxy, 2,4-dicarboxybutoxy, 1-carboxypentoxy, 5-carboxypentoxy, 1-carboxyhexyloxy, or 6-carboxyhexyloxy; amino$(C_1-C_6)$alkyl can be aminomethyl, 1-aminoethyl, 2-aminoethyl, 1-aminopropyl, 2-aminopropyl, 3-aminopropyl, 2,3-diaminopropyl, 1-aminobutyl, 4-aminobutyl, 2,4-diaminobutyl, 1-aminopentyl, 5-aminopentyl, 1-aminohexyl, or 6-aminohexyl; hydroxy$(C_2-C_6)$alkoxy can be 2-hydroxyethoxy, 3-hydroxypropoxy, 2-hydroxyisopropoxy, 4-hydroxybutoxy, 3,4-dihydroxybutoxy, 3-hydroxy-iso-butoxy, 4-hydroxy-sec-butoxy, 5-hydroxypentoxy, 4,5-dihydroxypentoxy, 6-hydroxyhexyloxy, 2,6-dihydroxyhexyloxy, 3,6-dihydroxyhexyloxy, 4,6-dihydroxyhexyloxy or 5,6-dihydroxyhexyloxy; aminocarbonyl$(C_1-C_6)$alkyl can be aminocarbonylmethyl, 1-(aminocarbonyl)ethyl, 2-(aminocarbonyl)ethyl, 1-(aminocarbonyl)propyl, 2-(aminocarbonyl)propyl, 3-(aminocarbonyl)propyl, 2,3-di(aminocarbonyl)propyl, 1-(aminocarbonyl)butyl, 4-(aminocarbonyl)butyl, 2,4-di(aminocarbonyl)butyl, 1-(aminocarbonyl)pentyl, 5-(aminocarbonyl)pentyl, 1-(aminocarbonyl)hexyl, or 6-(aminocarbonyl)hexyl; trifluoroacetylamino$(C_1-C_6)$alkyl can be trifluoroacetylaminomethyl, 1-(trifluoroacetylamino)ethyl, 2-(trifluoroacetylamino)ethyl, 1-(trifluoroacetylamino)propyl, 2-(trifluoroacetylamino)propyl, 3-(trifluoroacetylamino)propyl, 2,3-bis(trifluoroacetylamino)propyl, 1-(trifluoroacetylamino)butyl, 4-(trifluoroacetylamino)butyl, 2,4-bis(trifluoroacetylamino)butyl, 1-(trifluoroacetylamino)pentyl, 5-(trifluoroacetylamino)pentyl, 1-(trifluoroacetylamino)hexyl, or 6-(trifluoroacetylamino)hexyl; adamantyl$(C_1-C_6)$alkyl can be adamant-1-ylmethyl, 1-adamant-1-ylmethyl, 2-(adamant-1-yl)ethyl, 1-(adamant-1-yl)propyl, 2-(adamant-1-yl)propyl, 3-(adamant-1-yl)propyl, 2,3-di(adamant-1-yl)propyl, 1-(adamant-1-yl)butyl, 4-(adamant-1-yl)butyl, 2,4-di(adamant-1-yl)butyl, 1-(adamant-1-yl)pentyl, 5-(adamant-1-yl)pentyl, 1-(adamant-1-yl)hexyl, 6-(adamant- 1-yl)hexyl, adamant-2-ylmethyl, 1-adamant-2-ylmethyl, 2-(adamant-2-yl)ethyl, 1-(adamant-2-yl)propyl, 2-(adamant-2-yl)propyl, 3-(adamant-2-yl)propyl, 2,3-di(adamant-2-yl)propyl, 1-(adamant-2-yl)butyl, 4-(adamant-2-yl)butyl, 2,4-di(adamant-2-yl)butyl, 1-(adamant-2-yl)pentyl, 5-(adamant-2-yl)pentyl, 1-(adamant-2-yl)hexyl, or 6-(adamant-2-yl)hexyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_1-C_6)$alkanoyloxy can be formyloxy, acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

Specifically, $R_1$ is —O—Y.

Specifically, $R_1$ and $R_2$ together are oxo (=O).

Specifically, $R_3$ is hydrogen.

Specifically, $R_3$ is hydroxy, halo, carboxy, mercapto, $(C_1-C_6)$alkyl, $(C_1-C_6)$alkoxy, $(C_3-C_8)$cycloalkyl, or $(C_3-C_8)$cycloalkyloxy.

Specifically, $R_3$ is —O—Y.

Specifically, $R_4$ is methyl or hydroxymethyl.

Specifically, $R_5$ is methyl or hydroxymethyl;

Specifically, $R_4$ and $R_5$ are each methyl;

Specifically, $R_4$ is hydroxymethyl and $R_5$ is methyl;

Specifically, $R_6$ is hydrogen.

Specifically, $R_6$ is absent and the adjacent --- is a present.

Specifically, $R_7$, $R_8$, $R_9$ and $R_{10}$ are each independently hydrogen or methyl.

Specifically, $R_7$ is hydrogen, $R_8$ is methyl, $R_9$ is hydrogen and $R_{10}$ is methyl.

Specifically, $R_7$ is hydrogen, $R_8$ is hydrogen, $R_9$ is methyl and $R_{10}$ is methyl.

Specifically, $R_8$ and $R_{11}$ together are —O—C(=X)—;

Specifically, $R_{11}$ is methyl.

Specifically, $R_{11}$ is carboxy.

Specifically, X is two hydrogens or is oxo.

Specifically, the bond at positions 1 and 2 represented by --- is present.

Specifically, the bond at positions 1 and 2 represented by --- is absent.

Specifically, the bond at positions 12 and 13 represented by --- is present.

Specifically, the bond at positions X and X represented by --- is absent.

Specifically, Y is H.

Specifically, Y is O=P($R_b$)$_2$, or O=P($R_c$)$_2$OP(O)($R_d$)—.

Specifically, Y is —SO$_2$$R_a$, Si($R_e$)$_3$, or tetrahydropyran-2-yl.

Specifically, Y is an amino acid, a peptide, or a glycoside.

Specifically, Y is H, aryl, $(C_3-C_8)$cycloalkyl, adamantyl, —SO$_2$$R_a$ O=P($R_b$)$_2$, O=P($R_c$)$_2$OP(O)($R_d$)—, Si($R_e$)$_3$, tetrahydropyran-2-yl, an amino acid, a peptide, a glycoside, or a 1 to 10 membered branched or unbranched carbon chain optionally comprising 1, 2, or 3 heteroatoms selected from non-peroxide oxy, thio, and —N($R_f$)—; wherein said chain may optionally be substituted on carbon with 1,2,3, or 4 oxo (=O), hydroxy, carboxy, halo, mercapto, nitro, —N($R_g$)($R_h$), $(C_3-C_8)$cycloalkyl, $(C_3-C_8)$cycloalkyloxy, aryl, aryloxy, adamantyl, adamantyloxy, hydroxyamino, trifluoroacetylamino, a glycoside, an amino acid, or a peptide; and wherein said chain may optionally be saturated or unsaturated (e.g. containing one, two, three or more, double or triple bonds);

Specifically, Y is a 1 to 10 membered branched or unbranched carbon chain optionally comprising 1, 2, or 3 heteroatoms selected from non-peroxide oxy, thio, and —N($R_f$)—; wherein said chain may optionally be substituted on carbon with 1, 2, 3, or 4 oxo (=O), hydroxy, carboxy, halo, mercapto, nitro, —N($R_g$)($R_h$), $(C_3-C_8)$cycloalkyl, $(C_3-C_8)$cycloalkyloxy, aryl, aryloxy, adamantyl, adamantyloxy, hydroxyamino, trifluoroacetylamino, a glycoside, an amino acid, or a peptide; and wherein said chain may optionally be saturated or unsaturated.

Specifically, Y is $(C_1-C_{10})$alkyl, $(C_2-C_{10})$alkenyl, $(C_2-C_{10})$alkynyl, or $(C_1-C_{10})$alkanoyl, wherein any $(C_1-C_{10})$alkyl, $(C_2-C_{10})$alkenyl, $(C_2-C_{10})$alkynyl, or $(C_1-C_{10})$alkanoyl, is optionally substituted with hydroxy, carboxy, mercapto, —N($R_g$)($R_h$), $(C_3-C_8)$cycloalkyl, aryl, aryloxy, adamantyl, a glycoside, an amino acid, or a peptide.

Specifically, Y is $(C_1-C_{10})$alkyl or $(C_1-C_{10})$alkanoyl.

Specifically Y is aryl, $(C_3-C_8)$cycloalkyl, or adamantyl.

Specifically, Y is H, —C(=O)C(=O)$R_k$, —C(=O)$R_m$, —SO$_2$$R_n$O=P($R_o$)$_2$, O=P($R_p$)$_2$OP(O)($R_q$)—, $(C_1-C_6)$alkanoyl, Si(R)$_3$, (C=O)N(R)$_2$, benzyl, benzoyl, tetrahydropyran-2-yl, 1-[(C$_1$-C$_4$)alkoxy] $(C_1-C_4)$alkyl, an amino acid, a peptide, or a glycoside; wherein each R is H, phenyl or $(C_1-C_6)$alkyl; $R_k$ is hydroxy, $(C_1-C_6)$alkoxy, aryloxy, aryl$(C_1-C_6)$alkoxy, $(C_3-C_8)$cycloalkyloxy, hydroxy$(C_2-C_6)$alkoxy, adamantyloxy, $NR_rR_s$, an amino acid, a peptide, hydroxyamino, amino$(C_1-C_6)$alkyl or a glycoside; $R_m$ is aryl, carboxy$(C_1-C_6)$alkyl, aminocarbonyl$(C_1-C_6)$alkyl, trifluoroacetylamino$(C_1-C_6)$alkyl, amino $(C_1-C_6)$alkyl, vinyl, adamantyl, adamantyl$(C_1-C_6)$alkyl; $R_n$ is $(C_1-C_6)$alkyl or aryl; $R_o$, $R_p$, and $R_q$ are each independently hydroxy, $(C_1-C_6)$alkoxy, hydroxy$(C_2-C_6)$alkoxy, adamantyloxy, adamantyl$(C_1-C_6)$alkoxy, norbornyloxy, 1,1-di(hydroxymethyl)-2-hydroxyethoxy, carboxy$(C_1-C_6)$alkoxy, 2,3-epoxypropyloxy, benzyloxy, $(C_3-C_8)$cycloalkyloxy, $NR_vR_w$, or aryloxy; $R_r$ and $R_s$ are each independently hydrogen, $(C_1-C_6)$alkyl, hydroxy$(C_1-C_6)$alkyl, adamantyl, adamantyl$(C_1-C_6)$alkyl, amino$(C_1-C_6)$alkyl, aminosulfonyl, $(C_1-C_6)$alkanoyl, or aryl; or $R_r$ and $R_s$ together with the nitrogen to which they are attached are pyrrolidino, piperidino, or morpholino; and $R_v$ and $R_w$ are each independently hydrogen, $(C_1-C_6)$alkyl, $(C_1-C_6)$alkanoyl, aryl or benzyl; wherein each aryl of $R_k$, $R_m$-$R_s$, $R_v$, and $R_w$ may optionally be substituted by 1, 2, or 3 aminosulfonyl, carboxy, $NR_tR_u$, $(C_1-C_6)$alkyl, $(C_1-C_6)$alkoxy, hydroxy, halo, nitro, cyano, mercapto, carboxy, hydroxy$(C_1-C_6)$alkyl, halo$(C_1-C_6)$alkyl, trifluoromethoxy, $(C_1-C_6)$alkanoyl, $(C_1-C_6)$alkoxycarbonyl, $(C_1-C_6)$alkylthio, or $(C_1-C_6)$alkanoyloxy; and wherein $R_t$ and $R_u$ are each independently hydrogen, $(C_1-C_6)$alkyl, $(C_1-C_6)$alkanoyl, phenyl, or benzyl.

Specifically, Y is H, —C(=O)C(=O)$R_k$, —C(=O)$R_m$, —SO$_2$$R_n$ $(C_1-C_6)$alkanoyl, (C=O)N(R)$_2$, benzyl, benzoyl, an amino acid, a peptide, or a glycoside.

Specifically, Y is —C(=O)C(=O)$R_k$, —C(=O)$R_m$, $(C_1-C_6)$alkanoyl, (C=O)N(R)$_2$, benzyl, or benzoyl.

Specifically, Y is O=P(OH)$_2$ or O=P(OH)$_2$OP(O)(OH)—.

Specifically, Y is —SO$_2$$R_n$$(C_1-C_6)$alkanoyl, Si(R)$_3$, benzyl, benzoyl, tetrahydropyran-2-yl, or 1-[(C$_1$-C$_4$) alkoxy](C$_1$-C$_4$)alkyl.

Specifically, the compounds of the invention are useful to treat HSV-1, or HSV-2.

Specifically, $R_k$ can be hydroxy, $(C_1-C_6)$alkoxy, aryloxy, hydroxy$(C_2-C_6)$alkoxy, adamantyloxy, $NR_rR_s$, an amino acid, a peptide, amino$(C_1-C_6)$alkyl or a glycoside.

Specifically, $R_m$ can be aryl, carboxy$(C_1-C_6)$alkyl, aminocarbonyl$(C_1-C_6)$alkyl, trifluoroacetylamino $(C_1-C_6)$alkyl, amino$(C_1-C_6)$alkyl, adamantyl, or adamantyl$(C_1-C_6)$alkyl.

A preferred compound of formula (I) is a compound of formula (II):

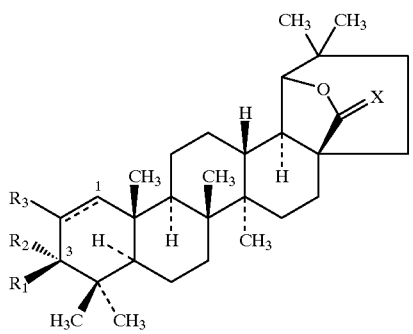

(II)

wherein $R_1$ to $R_3$ and X have any of the values, specific values or preferred values described herein; or a pharmaceutically acceptable salt thereof.

A preferred compound of formula II is a compound wherein one of $R_1$ and $R_2$ is hydrogen and the other is —O—Y, or $R_1$ and $R_2$ together are oxo (=O); $R_3$ is hydrogen, hydroxy, halo, carboxy, mercapto, ($C_1$–$C_6$)alkyl, ($C_1$–$C_6$)alkoxy, ($C_3$–$C_8$)cycloalkyl, or ($C_3$–$C_8$)cycloalkyloxy; the bond represented by --- is absent or is present; X is two hydrogens, or is oxo (=O) or thioxo (=S); and Y has any of the values, specific values or preferred values described herein; or a pharmaceutically acceptable salt thereof.

Another preferred compound of formula (I) is a compound of formula (III):

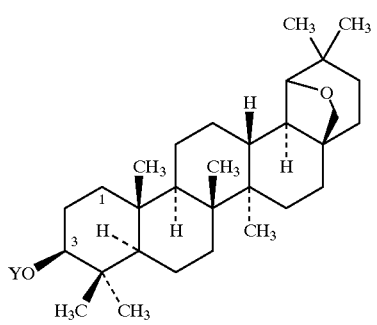

(III)

wherein Y has any of the values, specific values or preferred values described herein; or a pharmaceutically acceptable salt thereof.

A preferred value for Y is hydrogen, trifluoroacetyl, acetyl, trimethylsilyl, 4-methylphenylsulfonyl, or phosphono.

Another preferred value for Y is H, aryl, C(O)($C_1$–$C_6$) alkyl, C(O)($C_6$–$C_{10}$)aryl(COOH), C(O)($C_1$–$C_6$)alkyl (COOH), P(O)(Cl)$_2$, ($C_3$–$C_8$)cycloalkyl, adamantyl, —SO$_2$R$_a$, O=P(R$_b$)$_2$, O=P(R$_c$)$_2$OP(O)(R$_d$)—, Si(R$_e$)$_3$, tetrahydropyran-2-yl, an amino acid, a peptide, a glycoside, or a 1 to 10 membered branched or unbranched carbon chain optionally comprising 1, 2, or 3 heteroatoms selected from non-peroxide oxy, thio, and —N(R$_f$)—; wherein said chain may optionally be substituted on carbon with 1, 2, 3, or 4 oxo (=O), hydroxy, carboxy, halo, mercapto, nitro, —N(R$_g$) (R$_h$), ($C_3$–$C_8$)cycloalkyl, ($C_3$–$C_8$)cycloalkyloxy, aryl, aryloxy, adamantyl, adamantyloxy, hydroxyamino, trifluoroacetylamino, a glycoside, an amino acid, or a peptide; and wherein said chain may optionally be saturated or unsaturated (e.g. containing one, two, three or more, double or triple bonds);

A preferred compound of formula I for use in the methods of the invention is allobetulin or uvaol.

Methods of synthesizing allobetulin (19β, 28-epoxy-18α-olean-3β-ol) and certain analogs thereof from betulin and its corresponding analogs are known in the art (see Linkowska, E., *Triterpenoids, Part XI*. [1] *Isomerization of Betulin and its Derivatives*, Polish J. Chem., 68, 875–876 (1994)). Allobetulin can also be produced from betulin as disclosed herein.

Betulin (lup-20(29)-ene-3β, 28-diol) is commercially available from the Sigma Chemical Co., St. Louis, Mo. inter alia and is described, along with its diacetate in Merck 1212, *The Merck Index* (11th ed., 1989). See also, J. Simonsen et al., *The Terpenes*, Vol. IV, Cambridge U. Press (1957) at pages 187–328.

Compounds of formula I wherein Y is other than hydrogen can be prepared by methods known to the art, for example, by reaction of a corresponding alcohol with (a) silyl chlorides in the presence of organic amines, (b) (alkenyl)alkyl ethers under acid catalysis, (c) aroyl or alkanoyl anhydrides and organic bases, or (d) benzoyl chloride and base.

Many of the values for Y (e.g. —SO$_2$R$_n$, ($C_1$–$C_6$) alkanoyl, Si(R)$_3$, benzyl, benzoyl, tetrahydropyran-2-yl, or 1-[($C_1$–$C_4$)alkoxy]($C_1$–$C_4$)alkyl) are in the general class of "removable hydroxy protecting groups" and can thus be prepared form a corresponding compound of formula I wherein Y is hydrogen using techniques that are known in the art. For example, see Greene, T. W.; Wutz, P. G. M. "Protecting Groups In Organic Synthesis" second edition, 1991, New York, John Wiley & sons, Inc.

Compounds of formula I wherein Y is —C(=O)C(=O) R$_k$ can be prepared from a corresponding compound wherein Y is —C(=O)C(=O)Cl by reaction with an amine or alcohol of formula R$_k$—H.

Compounds of formula I wherein Y is —C(=O)R$_m$ can be prepared from a corresponding compound wherein Y is H by reaction with an acid chloride of formula ClC(=O)R$_m$.

Compounds of formula I wherein Y is ($C_1$–$C_6$)alkanoyl can be prepared from a corresponding compound wherein Y is H by reaction with the requisite ($C_1$–$C_6$)alkanoyl-Cl.

Monophosphates of formula I can be prepared using methods similar to those described in Vince et al. (U.S. Pat. No. 5,175,292).

Certain compounds of formula I have been isolated from natural sources or have been synthesized from related natural products. Some compounds of formula I, in particular, known compounds of formula I, can conveniently be used as starting materials for the preparation of other compounds of formula I. For example, the compounds allobetulin, uvaol, usuric acid and hederin hydrate can conveniently be used to prepare related compounds of formula I using techniques that are known in the art.

The compound 3-chlorooxalylallobetulin is a particularly useful intermediate for preparing compounds of formula III wherein Y is —C(=O)C(=O)R$_k$.

Pharmaceutically acceptable salts include nontoxic amine salts and alkali metal salts of phosphates and nontoxic inorganic and organic acid addition salts of amines, such as the citrate, malonate, maleate, tartarate, hydrochloride, sulfate, bicarbonate, and carbonate salts.

The compounds of formula (I) can be formulated as pharmaceutical compositions and administered to a mammalian host, such as a human patient afflicted with herpesvirus infection, in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusable solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. The liquid compositions can also be employed as eye drops, mouth washes, douches, etc. Antibacterial presaturated wipes are disclosed by Anderson (U.S. Pat. No. 4,896,768).

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Other examples of useful dermatological compositions which can be used to deliver the compounds of formula (I) to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula (I) can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula (I) in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%. Single dosages for injection, infusion or ingestion will generally vary between 50–1500 mg, and may be administered, i.e., 1–3 times daily, to yield levels of about 0.5–50 mg/kg, for adults.

Pharmacological Studies

A. Materials and Methods

1. Test Compounds

Stock solutions of the compounds used for the testing of antiviral activity against HSV-1 and HSV-2 were prepared in distilled water, filtered through 0.2 μm filter (Acrodisc®, Gelman Sciences, USA) and stored at room temperature until used. For comparative study, stock solutions of acyclovir (Sigma, USA) containing 250 ng/ml and 12,500 ng/ml of acycloguanosine were prepared in distilled water, filtered through 0.2 μm filter (Acrodisc®, Gelman Sciences, USA) and stored at 4° C. until use.

2. Cells

Human laryngeal epithelial carcinoma cells (HEp-2, ATCC, Rockville, Md.) were used for testing of antiviral compounds by cytopathic effect (CPE) inhibition and plaque reduction assay. Primary human foreskin fibroblast cells (HFF) obtained from Dr. E. R. Kern (Department of Pediatrics, University of Alabama Medical School, 309 Bevill Biomedical Research Building, 845 19th Street South, Birmingham, Ala., 35294–2170), were used for cytopathic effect (CPE) inhibition assay. HEp-2, African green monkey kidney cells (Vero, ATCC), HFF and primary rabbit kidney cells were used to determine the cytotoxic effect of compounds of formula I. These cells were propagated in Dulbeco's modified Eagle's medium (DMEM) (Sigma, USA) supplemented with 10% inactivated fetal calf serum (FCS), 25 mM HEPES, 0.2% sodium bicarbonate and 1% penicillin/-streptomycin at 37° C. in the presence of 5% $CO_2$.

3. Virus Strains

The antiviral activity of the test compounds was determined against HSV-1 strain F, HSV-2 strain G (ATCC), HSV-1 strain E-377 and HSV-2 strain MS (Dr. E. R. Kern, see above), CMV strain AD 169 (NIH), HCMV (NIH), MCMV (NIH), and VZV strain Ellen (NIH). Highly infective virus stocks of HSV-1 and HSV-2 were prepared by infecting a confluent monolayer of HEp-2 (ATCC) or HFF in 150 $cm^2$ plastic tissue culture flasks (Falcon, USA) at a multiplicity of infection of 0.5 in DMEM supplemented with 10% inactivated fetal calf serum and 1% penicillin/streptomycin at 37° C. in the presence of 5% $CO_2$. The infected cells were disrupted through three freeze/thaw cycles, and viruses were clarified from large cell debris by low speed centrifugation at 3000 rpm for 10 minutes. The virus suspension was separated, aliquoted and stored at –80° C. until assayed or used for animal infection. The stock HSV-1 (E377) and HSV-2 (MS strain) contained $3.5 \times 10^8$ and $1.1 \times 10^7$ pfu/ml respectively.

4. Antiviral Assays: Cytopathic Effect (CPE) Inhibition Assay

Low passage HFF cells were seeded into 96-well tissue culture plates 24 hours prior to use at a cell concentration of $2.5 \times 10^4$ cells per ml in 0.2 ml of DMEM supplemented with 10% fetal calf serum. After 24 hours of incubation at 37° C. in the presence of 5% $CO_2$, medium was removed and the test compounds were diluted two-fold in DMEM in the 96-well tissue culture plate containing monolayer. After dilution of the test compounds and acycloguanosine (Acyclovir®) in the respective wells, 100 μl of the appropriate virus concentration was added to each well, excluding cell control, which received 100 μl of DMEM. For both HSV-1 and HSV-2 assays, the virus concentration utilized was 1000 pfu/ml and for HCMV, MCMV, and VZV assay 2500 pfu/ml were used. The plates were then incubated at 37° C. in the presence of 5% $CO_2$ for two to three days for HSV-1 and HSV-2, 10 days for VZV and 14 days for HCMV and MCMV. The virus induced cytopathic effect (CPE) was monitored microscopically every day. CPE of HSV-1 was recognized by cell rounding and clumping, while HSV-2 formed large syncytia along with rounding and clumping of cells. Antiviral activity is expressed as the 50% effective concentration ($EC_{50}$), i.e., the concentration of test compound required to reduce viral CPE by 50%. $EC_{50}$s were estimated from graphical plots of percent CPE against the concentration of the test compounds. The $EC_{50}$s for each compound are the mean of $EC_{50}$s for three or more independent experiments. After three days of incubation period, media was aspirated and the cells stained with a 0.1% crystal violet solution for 30 minutes. The stain was then removed and the plates were rinsed with tap water, air dried and retained.

5. Antiviral Assays: Plaque Reduction Assay

HEp-2 cells were grown to monolayer in 24 well tissue culture plates in DMEM containing 10% fetal calf serum at 37° C. for 24–36 hours in the presence of 5% $CO_2$. The monolayer of HEp-2 cells was infected with 0.1 ml of HSV-1 (strain F) or HSV-2 (strain G) containing 100 pfu. The viruses were allowed to adsorb for 1 hour at 37° C. in the presence of 5% $CO_2$. All wells containing virus infected cells except virus control were overlaid with 0.9 ml of DMEM and 1 ml of test compound. The virus control and cell control received DMEM only. All microtiter plates were incubated at 37° C. in the presence of 5% $CO_2$ and observed twice daily for 72 hours for viral CPE. At the end of the experiment, plates were stained with 0.1% crystal violet and the results were quantified by counting plaque forming units.

6. Screening and Confirmation for Epstein-Barr Virus (EBV):

There are two prototypes of infectious Epstein-Barr Virus (EBV). One is exemplified by the virus derived from supernatant fluids of the P3HR-1 cell line. This cell line produces nontransforming virus that causes the production of Early Antigen (EA) after primary infection or superinfection of B cell lines. The other prototype is exemplified by the B-95-8 virus. This virus immortalized cord blood lymphocytes and induces tumors in marmosets. It does not, however, induce an abortive productive infection even in cell lines harboring EBV genome copies.

Romas is an exceptional B cell line derived from Burkitt's lymphoma tumor but containing no detectable EBV genome copies and is Epstein-Barr nuclear antigen complex (EBNA) negative. Romas/AW was obtained by in vitro infection of Romas with the P3HR-1 virus and contain one resident EBV genome copy/cell. Raji is a Burkitt's lymphoma cell line containing 60 EBV genome/cell, and was the primary cell used for screening antiviral activity against EBV early antigen (EA) expression. Daudi is a low level producer that contains 152 EBV genome copies/cell. It spontaneously expresses EBV EA in 0.25–0.5% of the cells. It was used in follow-up studies to confirm activity. These cell lines respond to superinfection by EBV by expressing EA-diffuse component EA (D), EA restricted component EA (R), and viral capsid antigen (VCA). All cell lines were maintained in RPMI-1640 medium supplemented with 10% FCS, L-glutamine and 100 μg/ml gentamicin. The cultures were fed twice weekly and the cell concentration was adjusted to $3 \times 10^5$/ml. The cells were kept at 37° C. in humidified atmosphere with 5% $CO_2$.

Cells were infected with the P3HR-1 strain of HBV and the test compound was added after adsorption (45 minutes at 37° C.) and washing of the cell cultures. The cultures were incubated for two days in complete medium to allow viral gene expression. Following the 48 hours of incubation, the numbers of cells of each sample was counted and smears were made. Monoclonal antibodies to the different EA components and VCA were then added to the cells and then incubated and washed. This is followed by a fluorescein conjugated rabbit anti-mouse IgG antibody, and the number of fluorescence cells in the smear were counted. The total number of cells in the cultures positive for EA or VCA were then calculated and compared.

7. Cell Proliferation Assay (Cytotoxicity)

HFF, Vero and HEp-2 cells were seeded in 24-well tissue culture plates at a concentration of $2.5 \times 10^6$ cells per well in DMEM containing 10% FCS and incubated for 24 hours at 37° C. in the presence of 5% $CO_2$. To the monolayer of these cells 0.5, 1.0, 1.5 and 2.0 ml of solution of antiviral compounds were added in the respective wells in duplicate and the cells were then incubated in a 5% $CO_2$ incubator at 37° C. for 72 hours. The cells were observed daily for any change in morphology. The rounding and lysis of cells were observed if the compound has cytotoxic effect. At the end of this time, the media-drug solution was removed and the cells washed. One ml of 0.25% trypsin was added to each well and incubated until the cells start to come off of the plate. The cells-media mixture was then pipetted up and down several times to resuspend the cells and 0.2 ml of the cell suspension was added to 9.8 ml of trypan blue and cells were counted using hemocytometer. Each sample was counted three times with three replicate wells per sample.

8. Effect of Betulin and Allobetulin Treatment on the Cutaneous HSV-1 and HSV-2 Infection in Rats and Cutaneous HSV-1 and Vaginal HSV-2 Infection in the Guinea Pigs Female Sprague Dawley Rats, 60 days old approximately 175 to 199 grams each, were obtained from Harlan Inc., Indianapolis, Ind. Female Hartley outbred guinea pigs 26 days old and weighing approximately 350 to 400 grams each were obtained from Charles River Breeding Labs, Wilmington, Mass. The animals were housed singly and given feed and water ad lib.

9. Betulin, Allobetulin and Acyclovir® Preparation

2% Betulin and allobetulin ointment were prepared aseptically in polyethylene glycol (PEG) as ointment base and stored at room temperature until used. Acyclovir® (Zovirax® Ointment, Glaxo Wellcome Inc., Research Triangle Park, N.C.) containing 5% acycloguanosine in PEG was purchased for this study.

10. Virus Inoculation Procedure: Cutaneous Herpes in Rats and Guinea Pigs

Rats or guinea pigs were anesthetized with isoflurane (Rhone-Poulenc, Bristol, UK) liquid inhalation. Hairs from both flanks were removed with an electric hair clipper. The remaining hairs were removed by applying a chemical depilatory lotion (Nair® Hair Removing Lotion). The exposed area of the skin was then washed twice with lukewarm water and dried. After four hours, the animals were infected by placing one drop of virus suspension containing $1 \times 10^4$ pfu at three different sites on each of the left and right flank, and was then slightly scarified with Greer Derma Pick® Skin Testing System (Greer Labs, Lenoir, N.C.). All of the inoculation sites were activated eight times for entry of virus particles into the dermal layer. HSV-1 (E377) and HSV-2 (MS Strain) virus suspensions containing $8.5 \times 10^7$ and $1.1 \times 10^7$ pfu/ml respectively, were used.

11. Treatment Procedure: Cutaneous Herpes in Rats and Guinea Pigs

The treatment of infected rats or guinea pigs started beginning 18 hours after virus infection and continued for 3 days. The right flanks of infected rats from different trial groups were treated twice daily with 2% betulin, 2% allobetulin and 5% acycloguanosine (Zovirax®, Acyclovir®, Glaxo Wellcome Inc., Research Triangle Park, N.C.) according to the experimental protocol. Ointment preparations were applied by a sterile wooden stick applicator. The left flanks of the same animals were placebo treated with ointment base. Besides test groups, each experiment included HSV-1 (E377) and HSV-2 (MS strain) infected and uninfected scarified placebo controls. The animals were observed daily for severity of infection for 10 days. Variables assessed were erythema around the site of infection, pustule formation, size, number and whether confluent, induration and scab formation on a 0, +1, +2, +3, +4 scale with increment of 0.5 as described by Kern et al., 1978 (20Photographs of the animals were taken before scarification, after scarification and infection, during treatment, and at the end of treatment. Virus specimens were taken from the infected sites by using Dacron Swabs (Hardwood Products Co., Guilford, Me.) in 1.0 ml DMEM tissue culture medium (Sigma, USA) after infection, during treatment and 3 days later. The swabs were stored at −80° C. until analyzed by CPE in HFF cells. The animals were kept for 20 days before euthanization, and observed daily for the recurrence of infection.

12. Virus Inoculation Procedure: Genital Heres Infection in Guinea Pigs

Female guinea pigs weighing 200 g were inoculated intravaginally with HSV-2 (MS strain). One hour before viral inoculation the animals were swabbed using Dacron-polyester tipped applicator moistened in sterile saline to remove vaginal secretions. The animals were then infected with one drop of HSV-2 suspension containing $1 \times 10^4$ pfu, and the surface of the vaginal mucosa was slightly scarified with a sterile Greer Derma Pick® Skin Testing System (Greer Labs, Lenoir, N.C.).

13. Treatment Procedure: Vaginal Herpes in Guinea Pigs

The treatment of infected guinea pigs was started 18 hours after infection and continued twice daily for 3 days. The 2% betulin and allobetulin ointment preparation was applied by sterile cotton swab. Each experiment included uninfected control, infected and placebo controls. The animals were observed daily for the infection, if any for 10 days. Photographs of the vaginal area were taken before infection, after infection, during treatment, 5 and 7 days after treatment. Virus specimens were taken from the infected sites by using Dacron Swabs (Hardwood Products Co., Guilford, Me.) in 1.0 ml DMEM tissue culture medium (Sigma) after infection, during treatment and 3 days later. The swabs were stored at −80° C. until analyzed. The virus content of the specimens was measured by plaque assay in HEp-2 cells and the mean virus titer was calculated. The animals were kept for 20 days before euthanization, and observed daily for the recurrence of infection. The variable assessed was typical HSV vesicle formation, size, number and whether confluent, induration at the site of infection and scab formation.

B. Results

1. Antiviral Effect on HSV-1

Allobetulin, uvaol, ursolic acid, hederin hydrate and other representative compounds of formula I were tested for antiviral activity against HSV-1 (E377). The compounds varied in potency and selectivity. The qualitative CPE inhibition assay (Table 1a and 2a) showed that betulin and allobetulin had significant anti HSV-1 activity in HEp-2 cells, while betulin have significant anti-HSV-1 activity in HFF cells. The $EC_{50}$'s and the corresponding selectivity indices of the test compounds, determine by CPE inhibition in HFF are presented in Table 1b. The $EC_{50}$ for betulin and allobetulin were found to be in the rage of 250 ng/ml and 300 ng/ml as compared to 1600 ng/ml for Acyclovir®. The plaque reduction assay in HEp-2 cells (Table 2b) showed that HSV-1 produced no plaque in 125 ng/ml of betulin and 12,500 ng/ml of for Acyclovir® treated cells as compared to 5 pfu in HSV-1 infected control cells. Allobetulin 3-phosphate and allobetulin lactone showed significant activity against HSV-1 (E377) in HFF cells.

2. Antiviral Effect on HSV-2

HSV-2 strain MS (NIH) and G (ATCC) were evaluated for their susceptibility to betulin, as well as to allobetulin and other compounds of formula (I) in primary human foreskin fibroblast (HFF) and HEp-2 cells. As noted for the HSV-1, the qualitative CPE inhibition assay (Tables 1a and 2a) showed that betulin and allobetulin have significant anti HSV-2 activity in HFF and HEp-2 cells. The EC50's of the test compound, determined by CPE inhibition in HFF are presented in Table 1b. The EC50 for betulin and allobetulin were found to be in the range of 125 ng/ml and 225 ng/ml respectively as compared to 6000 ng for Acyclovir®. The plaque reduction assay in HEp-2 cells showed that the number of plaques in 125 ng/ml of betulin, 150 ng/ml allobetulin and 12500 ng/ml Acyclovir® treated cells were found to be 16 pfu/$10^5$ cells, 17 pfu/$10^5$ cells and 30 pfu/$10^5$ cells respectively as compared to 47 pfu/$10^5$ cells in HSV-2 infected control cells (Table 2b). Compounds of formula (I) also demonstrated significant anti HSV-2 activity against both strains of viruses in HFF and Hep-2 cells.

Allobetulin has less antiviral effect against HSV-1 and HSV-2 as compared to betulin. However, allobetulin have significantly more effect against HSV-2 as compared to HSV-1 in human foreskin fibroblast cells.

3. Antiviral Effect on HCMV, VZV and EBV

Representative compounds of formula I were also tested against other herpes viruses in human foreskin fibroblast cells by CPE inhibition and found to have significant activity (Table 3).

4. Cytotoxicity Assay

The cytotoxicity assay performed in HFF cell lines showed that betulin and allobetulin were more toxic as compared to Acyclovir® at the effective dose concentration (Tables 1a and 1b). The $CC_{50}$ for betulin and allobetulin were found to be 250 ng/ml and 300 ng/ml as compared to >12,500 ng for Acyclovir® while $CC_{50}$ for the allobetulin derivatives were found to be almost the same as that of parent compound. Betulin, allobetulin and derivatives showed less cytotoxicity in HEp-2 cells (Table 2a). Less cytotoxicity was also observed in Vero and Rabbit kidney cell lines. In Vero cell line, the $CC_{50}$ for betulin and allobetulin were found to be 125 ng/ml and 300 ng/ml respectively (Table 4). No cytotoxicity was found in primary rabbit kidney cell line for betulin, allobetulin or Acyclovir®.

TABLE 1a

Effect against HSV-1 and HSV-2 Viruses in Human Foreskin Fibroblast Cells

| Compound | Conc. (ng/ml) | Qualitative Cytotoxic Effect at 2.0 ml dose | Qualitative CPE at 2.0 ml dose HSV-1 E377 | HSV-2 MS |
|---|---|---|---|---|
| Test Compounds: | | | | |
| Betulin | 125 | – | +++ | + |
| Allobetulin | 150 | – | +++ | ++ |
| Allobetulon | 150 | – | +++ | +++ |
| Allobetulon-1,2-ene-2-ol | 110 | – | +++ | +++ |
| 3β-Acetoxy-19αH-19,28lactone-oleanan | — | + | +++ | ++ |
| Acyclovir | 250 | – | +++ | +++ |
| | 12500 | – | + | + |
| HSV-1 Virus Control | | | +++ | |
| HSV-2 Virus Control | | | | +++ |
| Cell Control | | – | – | – |

Cytopathic Effect: Rounding, clumping of cells and syncytia formation
+++ = Complete cytopathic effect
++ = Moderate cytopathic effect
+ = Minimum cytopathic effect
– = No cytopathic effect
Cytotoxicity: Rounding and lysis of cells
+++ = Complete cytotoxicity
++ = Moderate cytotoxicity
+ = Minimum cytotoxicity
– = No cytotoxicity TABLE 1b Effect against HSV-1 and HSV-2 Viruses in Human Foreskin Fibroblast Cells

| Compound | Conc. (ng/ml) | $CC_{50}$ (ng/ml) | $EC_{50}$ (ng/ml) HSV-1 E377 | HSV-2 MS |
|---|---|---|---|---|
| Test Compounds: | | | | |
| Betulin | 125 | 250 | 250 | 125 |
| Allobetulin | 150 | 300 | 300 | 225 |
| Allobetulin Succinate | 125 | >250 | >250 | >250 |
| Allobetulin ethanolamine | 125 | 200 | >250 | >250 |
| Allobetulin ethanolamine chlorohydrate | 125 | 125 | 125 | 125 |
| Allobetulin 3-phosphate | 125 | >125 | >250 | 250 |
| Allobetulin lactone | 125 | >125 | >125 | 200 |
| Allobetulon | 150 | 300 | 300 | 300 |
| Allobetulon-1,2-ene-2-ol | 110 | 220 | 220 | 165 |
| Allobetulin 3-phthalate | 125 | >250 | >250 | 250 |
| Allobetulin 3-glycolate | 125 | >250 | >250 | 125 |
| Hederine hydrate | 125 | >250 | >250 | >250 |
| 3β-Acetoxy-19αH-19,28lactone-oleanan | 125 | 225 | 225 | 125 |
| Uvaol | 125 | 125 | >250 | >250 |
| Acyclovir ® | 12500 | >12500 | 1600 | 6000 |

$EC_{50}$ (50% antiviral effective dose) is the concentration of the test antiviral compound solution required to reduce viral plaques or CPE by 50%.
$CC_{50}$ (50% cell cytotoxic concentration) is the amount of test antiviral compound required to reduce the growth of uninfected cell by 50%.
Selectivity Index (SI) is the ratio of $CC_{50}$ for cell growth to $EC_{50}$ for viral CPE.

TABLE 2a

Effect against HSV-1 and HSV-2 Viruses in HEp-2 Cells

| Compound | Conc. (ng/ml) | Cyto-toxicity | Cytopathic Effect (CPE) Inhibition HSV-1 Strain F | HSV-2 Strain G |
|---|---|---|---|---|
| Test Compounds: | | | | |
| Betulin | 125 | − | + | + |
| Allobetulin | 150 | − | ++ | ++ |
| Allobetulin Succinate | 125 | − | ++ | + |
| Allobetulin 3-phosphate | 125 | − | +++ | ++ |
| Allobetulin lactone | 125 | − | +++ | ++ |
| Allobetulon | 125 | − | ++ | ++ |
| Allobetulon-1,2-ene-2-ol | 125 | − | ++ | ++ |
| Allobetulin 3-phthalate | 125 | − | ++ | ++ |
| Allobetulin 3-glycolate | 125 | − | +++ | ++ |
| Ursolic acid | 500 | − | ++ | ++ |
| Hederine hydrate | 125 | − | ++ | ++ |
| 3β-Acetoxy-19αH-19,28lactone-oleanan | 48 | − | ++ | ++ |
| Uvaol | 125 | − | ++ | ++ |
| Acyclovir | 12500 | − | +++ | +++ |
| HSV-1 Control | | | +++ | |
| HSV-2 Control | | | | +++ |
| Cell control | | | − | − |

Cytopathic Effect: Rounding, clumping of cells and syncytia formation
+++ = Complete cytopathic effect
++ = Moderate cytopathic effect
+ = Minimum cytopathic effect
− = No cytopathic effect
Cytotoxicity: Rounding and lysis of cells
+++ = Complete cytotoxicity
++ = Moderate cytotoxicity
+ = Minimum cytotoxicity
− = No cytotoxicity TABLE 2b Effect against HSV-1 and HSV-2 Viruses in HEp-2 Cells

| Compound | Conc. (ng/ml) | Plaque Reduction Assay Average pfu/$10^5$ Cells *HSV-1 Strain F | HSV-2 Strain G |
|---|---|---|---|
| Test Compounds: | | | |
| Betulin | 125 | 0 | 16 |
| Allobetulin | 150 | N/P | 17 |
| Uvaol | 38 | 0 | 28 |
| Ursolic acid | 900 | N/P | 33 |
| Hederin Hydrate | 500 | N/P | 38 |
| Acyclovir | 250 | N/P | 42 |
|  | 12500 | 0 | 30 |
| HSV-1 Virus Control | | 5 | |
| HSV-2 Virus Control | | | 47 |
| Cell Control | | | |

N/P = Plaque Reduction Assay not performed.

TABLE 3

Effect of Betulin and its Derivatives against Human Cytomegalovirus, Mouse Cytomegalovirus, Varicella-Zoster and Epstein-Barr Virus

| Virus | Test Compounds in DMSO | CPE inhibition in stationary cells (visual) in HCMV, MCMV, VZV VCA in EBV $EC_{50}$ ng/ml | $CC_{50}$ ng/ml | SI |
|---|---|---|---|---|
| Human Cytomegalovirus in HFF cells | Betulin | 2.9 | 14.2 | 4.9 |
| | Betulin succinate | 3.9 | 96.9 | 24.8 |
| | Betulin glycerol oxalate | >100.00 | >100.00 | 0.0 |
| | Uvaol | >100.0 | >100.0 | 0.0 |
| | Ursolic acid | >100.0 | >100.0 | 0.0 |
| | Hederine hydrate | >4.0 | 10.0 | <2.5 |
| | Ganciclovir ® | 100.0 | >100000 | >1000 |
| Mouse Cytomegalovirus MEF cells | Betulin | >20.0 | 80.0 | <4.0 |
| | Betulin succinate | >4.0 | 14.0 | <3.5 |
| | Ganciclovir ® | 900 | >100000 | 111.1 |
| Varicella-Zoster Virus HFF cells | Betulin | >4.0 | 14.1 | <3.5 |
| | Betulin succinate | >20.0 | 68.8 | <3.4 |
| | Betulin glycerol oxalate | >20.0 | 63.5 | <3.2 |
| | Betulin diphosphate | >100.0 | >100.0 | 0.0 |
| | Uvaol | >20.0 | 48.9 | <2.4 |
| | Ursolic acid | >0.8 | 2.9 | <3.6 |
| | Hederine hydrate | >4.0 | 11.5 | <2.9 |
| | Acyclovir ® | 3300 | >100000 | >30.3 |
| Epstein-Barr Virus Daudi cells | Betulin succinate | >50.0 | >50.0 | 0.0 |
| | Betulin glycerol oxalate | 7.2 | >50.0 | >6.9 |
| | Betulin diphosphate | 0.39 | >50.0 | >128.0 |
| | Uvaol | 0.31 | 44.3 | 142 |
| | Ursolic acid | 48.5 | >50.0 | >1.0 |
| | Hederine hydrate | 1.5 | 3.8 | 2.5 |
| | Acyclovir ® | 1400 | >100000 | >71.4 |

$EC_{50}$ (50% antiviral effective concentration) is the concentration of the test antiviral compound required to reduce viral plaques or CPE by 50%.
$CC_{50}$ (50% cell cytotoxic concentration) is the concentration of test antiviral compound required to reduce the growth of uninfected cell by 50%.
Selectivity Index (SI): Ratio of $CC_{50}$ for cell growth to $EC_{50}$ for viral CPE i.e., ($CC_{50}/EC_{50}$ ratio).
MCMV: Mouse Cytomegalovirus* $CC_{50}$ = 80.0

TABLE 4

Cytotoxic Effect in Rabbit Kidney and Vero Cell Lines

| Cell Line | $CC_{50}$ (ng/ml) Betulin | Allobetulin | Acyclovir |
|---|---|---|---|
| Primary Rabbit Kidney | >250 | >300 | >250 |
| Vero | 125 | 300 | 250 |

The results demonstrate that allobetulin is generally not toxic to human epithelial cells, African green monkey kidney cells, primary rabbit kidney cells and human foreskin fibroblast cells at concentrations sufficient to exhibit antiviral activity. These cells were used as indicator cells to test the effectiveness of allobetulin as compared to acyclovir (ACV) and betulin against HSV-1 and HSV-2 infection.

5. Antiviral Effect of Betulin and Allobetulin on the Cutaneous HSV-1 and HSV-2 Infection in the Rats The topical application of 2% betulin ointment twice daily for 3 days diminished the signs of the infectious process in HSV- I infected animals, as the number of typical HSV lesions decreased rapidly by the $4^{th}$ to $8^{th}$ days of infection, but the overall results were not significantly different from that of the 5% Acyclovir® ointment treated group which also showed the same healing response. In the HSV-1 infected placebo treated and untreated control rats the lesions persisted for seven to ten days, while in scarified uninfected control group there were no signs of scarification at the end of day 4 of scarification. In almost all of the treated and untreated control animals the clinical signs disappeared after 12–15 days of virus inoculation. Topical application of 2% betulin ointment was found to have significant effect against HSV-2 cutaneous infection as compared to HSV-1. Allobetulin ointment treatment was found to have moderate effect against HSV- 1 and HSV-2 infection in the rats.

6. Antiviral Effect of Betulin and Allobetulin on the Cutaneous HSV-1 Infection in Guinea Pigs As noted earlier for HSV-1 infection in rats, most of the infected guinea pigs showed typical HSV vesicular lesions on their skin from 3 to 4 days of virus inoculation. None of these guinea pigs died of HSV infection, and clinical signs disappeared from 12 to 15 days after inoculation. Topical application of 2% betulin and 5% Acyclovir® ointment twice daily for 3 days diminished the development of the clinical infectious process, but the overall results indicated that there was no significant difference among the betulin and Acyclovir® treated groups. Treatment with 2% allobetulin ointment was found to have moderate effect as compared to 2% betulin and 5% Acyclovir®.

7. Antiviral Effect of Betulin and Allobetulin on the Vaginal HSV-2 (MS) Infection in Guinea Pigs Significant effect of 2% betulin ointment treatment was observed in the vaginal HSV-2 infection of guinea pigs. Typical lesions and virus content in the infected vaginal area decreased significantly by 6 to 8 days of 2% betulin ointment treatment, twice daily for 3 days beginning 18 hours after infection. However 2% allobetulin ointment treatment was found to have moderate effect as compared to 2% betulin and 5% Acyclovir®.

The invention will be further described by reference to the following non-limiting examples.

EXAMPLE 1

Betulin

Silica (60–100 mesh) (0.3 kg) and 1.0 kg of coarsely ground dry birch bark (Minnesota paper birch) were successively loaded into a Soxhlet apparatus. The lower silica layer was separated from the birch bark with a paper filter. The extractor was supplied with a heated 4 liter Erlenmeyer flask and two doubled-jacked condensers. After 15 hours of extraction with refluxing chloroform (2l), the yellow chloroform solution was cooled to ambient temperature for 4 hours and the crystals were isolated by filtration. The resulting white crystalline material was recrystallized twice from chloroform to give betulin (80–110 g, 8%–11% yield, >97% pure, m.p., 256–257° C.). For biological studies, the betulin was recrystallized from iso-propanol (yield 60–65%, m.p. 260–261° C.).

EXAMPLE 2

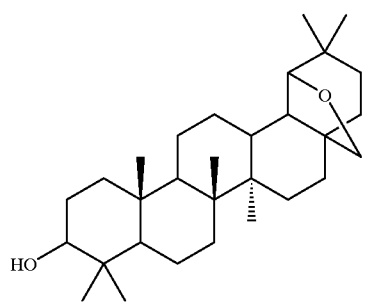

Allobetulin

Trifluoroacetic acid (5 ml, 99%) was added to betulin (2 g) in 50 ml of dichloromethane at 0° C. The resulting solution was stirred for 30 minutes, poured into 100 ml of cracked ice, extracted with $CH_2Cl_2$ (3×10 ml), washed with concentrated $NaHCO_3$ (2×20 ml) and water (2×20 ml), and dried over anhydrous $Na_2SO_4$. Evaporation of the solvent gave allobetulin, which was recrystallized from hexane-dichloromethane to yield white needles (yield 1.98 g, mp 268–269° C. [lit. 265–268° C.]); IR (KBr) 3448.5, 2941.5, 2866.6, 1780.7, 1456.6, 1384.4, 1168.9, 1035.0, $cm^{-1}$; 1H NMR ($CDCl_3$) δ 3.75 (D, J=10.3 Hz, 1H, 28-H), 3.51 (S, 1H, 19-H), 3.41 (D, J=10.3 Hz, 1H, 28-H), 3.18 (DD, 1H, 3-H), 0.74, 0.76, 0.81, 0.88, 0.89, 0.94, 0.94 (all S, 7×3H, 27-, 23-, 24-, 25-, 26-, 29-, 30-Me), 1.01–1.74 (complex CH—, $CH_2$, 25H); 13C NMR ($CDCl_3$) δ 88.41, 79.38, 71.49, 55.77, 51.35, 47.07, 40.99, 40.88, 40.87, 39.16, 37.52, 36.95, 36.51, 34.40, 34.18, 32.96, 29.08, 28.27, 27.57, 26.72, 26.72, 26.50, 24.82, 21.26, 18.54, 16.79, 15.96, 15.72, 13.82; MS (EI) 442, 424, 411, 371, 355, 303, 273, 257, 245, 231, 220, 207, 203, 189, 177, 162, 149, 135.

EXAMPLE 3

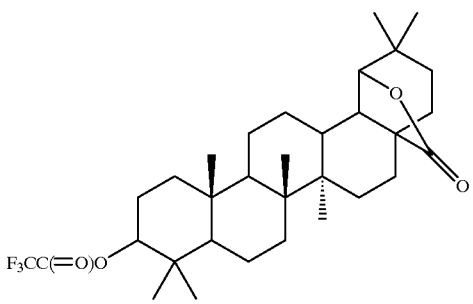

Allobetulin-3-Trifluoroacetyl Lactone

Trifluoroacetic acid (10 ml, 99%) was added to betulin (2 g) in 50 ml of $CH_2Cl_2$ at 0° C. After 15 minutes, trifluoroacetic anhydride (0.97 g) was added, the cooling bath was removed, and the solution was allowed to stir for 35 minutes. Powdered $NaBrO_3$ (2.56 g) was added, the mixture was allowed to stir for 16 hours at room temperature, and was then poured into 100 ml of cracked ice. The organic phase was separated and the aqueous phase was washed with dichloromethane (3×10 ml). The combined organics were extracted with 10% aqueous $NaHSO_3$ (2×30 ml) and water (2×20 ml), dried over $Na_2SO_4$ (anh.), and evaporated to give 2.4 g of Allobetulin-3-trifluoroacetyl lactone, which was recrystallized from hexane-chloroform to yield white needles; IR (KBr) 2946, 2867, 1768, 1467, 1447, 1389, 1219, 1168, 1067, 966, 922 cm$^{-1}$, $^1$H NMR (CDCl$_3$) δ 4.68(DD, 1H, 3H), 3.94 (S, 1H, 19H), 1.028, 0.961, 0.922, 0.895, 0.895, 0.895, 0.88 (all S, 7×3H, 23-, 24-, 25-, 26-, 27-, 29-, 30-Me), 1.1–1.9 (complex CH—, CH$_2$—, 24H); $^{13}$C NMR (CDCl$_3$) δ 180.05, 157.72(Q,), 114.92(Q), 86.418, 86.235, 55.696, 51.382, 46.937, 46.354, 40.838, 40.212, 38.703, 38.324, 37.406, 36.255, 33.814, 33.814, 32.568, 32.181, 28.997, 28.145, 27.992, 26.687, 25.784, 24.188, 23.474, 21.2, 18.227, 16.843, 16.478, 15.771, 13.891.

EXAMPLE 4

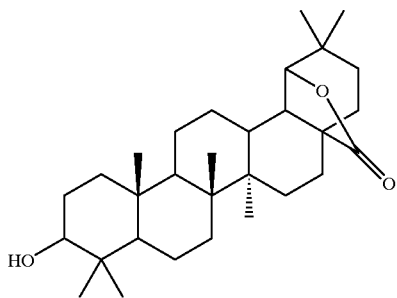

Allobetulin-Lactone

Allobetulin-3-trifluoroacetyl lactone (2 g) and potassium hydroxide (0.723 g) in 50 ml of CH$_3$OH were allowed to reflux for 4 hours. The methanol was evaporated and the mixture was diluted with 100 ml of cold water. The resulting precipitate ws filtered, washed with water (3×50 ml), dried in an oven at 100° C. and recrystallize from hexane-dichloromethane to yield white needles; $^1$H NMR (CDCl$_3$) δ 3.97(S, 1H, 19H), 3.22(DD, 1H, 3H), 1.057, 1.000, 0.987, 0.942, 0.903, 0.87, 0.791 (all S, 7×3H, 23-, 24-, 25-, 26-, 27-, 29-, 30-Me), 1.1–1.9 (complex CH—, CH$_2$—, 24H); $^{13}$C NMR (CDCl$_3$) δ 180.207, 86.316, 79.174, 55.791, 51.528, 47.01, 46.413, 40.853, 40.212, 39.177, 37.552, 36.313, 34.018, 33.843, 32.619, 32.232, 29.055, 28.254, 28.188, 27.642, 26.826, 25.842, 24.261, 21.178, 18.46, 16.85, 15.822, 15.669, 13.964.

EXAMPLE 5

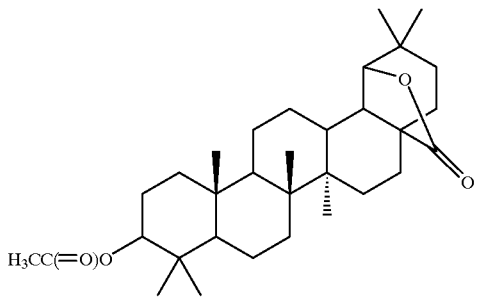

Allobetulin-3-acetyl lactone (3β-Acetoxy-19αH-19, 28-lactone-oleanane)

Trifluoroacetic acid (10 ml, 99%) was added to 3O-acetyl betulin (2 g) in 50 ml of CH$_2$Cl$_2$ at 0° C. After 10 minutes, powdered NaBrO$_3$ (2.2 g) was added and the mixture was allowed to stir for 6 hours. The mixture was poured into 100 ml of cracked ice and the organic phase was separated. The aqueous phase was extracted with dichloromethane (3×10 ml), and the combined organic extracts were washed with 10% aqueous NaHSO$_3$ (2×30 ml), 5% aqueous NaHCO$_3$ (2×30 ml) and water (2×20 ml), dried over Na$_2$SO$_4$ (anh.), and evaporated to give 2.08 g of 3-O-acetyl allobetulin-lactone, which was recrystallized from hexane-dichloromethane to yield white needles mp. 312.5–315.4° C. (dec); IR (KBr) 2943, 2878, 1761, 1729, 1502, 1486, 1446, 1374, 1252 cm$^{-1}$; $^1$H NMR (CDCl$_3$) δ 4.50 (DD, 1H, 3H), 3.94 (S, 1H, 19H), 2.03 (S, 3H, Ac—Me), 1.04, 0.97, 0.95, 0.8, 0.8, 0.79, 0.78 (all S, 7×3H, 23-, 24-, 25-, 26-, 27-, 29-, 30-Me), 1.02–1.79 (complex CH—, CH$_2$—, 23H); $^{13}$C NMR (CDCl$_3$) δ 13.899, 15.779, 16.741, 16.879, 18.307, 21.164, 21.601, 23.896, 24.210, 26.745, 25.784, 28.158, 28.159, 29.004, 32.181, 32.568, 33.792, 33.916, 36.284, 37.428, 38.055, 38.878, 40.175, 46.420, 40.831, 46.959, 51.419, 55.835, 180.352, 81.244, 86.381, 171.579; MS (EI) 482, 438, 424, 395, 356, 327, 281, 253, 207, 189, 174, 162, 147, 135, 121.

EXAMPLE 6

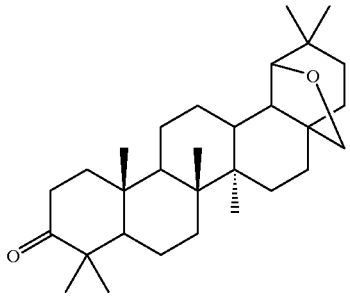

Allobetulon

Dry DMSO (22 mmol, 1.76 g) in 25 ml of dry dichloromethane was added drop wise over 3–5 minutes to a solution of COCl$_2$ (11 mmol, 1.397 g) in 25 ml of dry dichloromethane at −50–60° C. (I-Pr alcohol—dry ice bath). After 5 minutes, crystals of allobetulin (10 mmol, 4.43 g) were added and the solution was allowed to stand for 30 minutes. Triethylamine (25-mmol, 2.53 g) was added and the temperature was allowed to increase to 10° C. The solution was poured into 100 ml of cracked ice, extracted with dichloromethane (3×20 ml) and washed with water (5×10 ml), 5% HCl(2×10 ml), and H$_2$O(2×10 ml). The organics were dried over sodium sulfate and evaporated to give 4.5 g of crude compound. Column chromatography (hexane: ether=80:20) gives 4.31 g of white crystals mp. 228.8–235.1 ° C.; IR (KBr) 2949, 2859, 1774, 1702, 1457, 1382, 1167, 1034 cm$^{-1}$; $^1$H NMR (CDCl$_3$) δ 3.74 (D, J=10.3 Hz, 1H, 28-H), 3.48 (S, 1-H, 19-H), 3.39 (D, J=10.3 Hz, 1H, 28-H), 2.37 (M, 2H, 2-H, H), 1.85 (M, 1H, 19-H), 0.72, 0.81, 0.81, 0.815, 0.91, 0.92, 0.99 (all S, 7×3H, 27-, 23-, 24-, 25-, 26-, 29-, 30-Me), 1.01–1.54 (complex CH—,CH$_2$, 25H,); $^{13}$C NMR (CDCl$_3$) δ 218.08, 88.01, 71.39, 55.08, 50.55, 47.43, 46.92, 41.60, 40.91, 40.68, 39.97, 37.11, 36.88, 36.43, 34.41, 34.23, 33.33, 32.86, 29.00, 26.92, 26.60, 26.40, 24.73, 21.68, 21.16, 19.79, 16.52, 15.68, 13.63; MS(EI) 440, 422, 411, 369, 355, 281, 220, 207, 205, 191, 177, 163, 149, 135, 121;

EXAMPLE 7

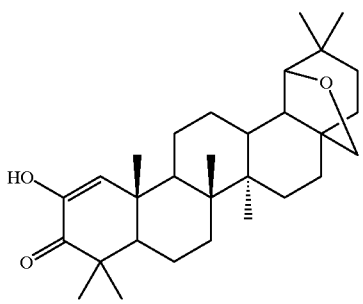

Allobetulon 1,2-ene-2-ol.

To a solution of allobetulon (1.8 g) in dry benzene, tert-butyl alcohol (1:1, 40 ml) was added a solution of potassium tert-butoxide (1.2 g) in tert-butyl (20 ml) and oxygen was bubbled into the stirred mixture for 1.5 hours. The mixture was acidified with 2.5 ml of glacial acetic acid and extracted with $CH_2Cl_2$. After washing with water (2×15 ml), 5% aqueous $NaHCO_3$ (2×30 ml) and water (30 ml), the extract was dried over $Na_2SO_4$ and evaporated to give crystals, which after chromatography on silica gel (hexane:ether=85:15) yield white crystalline compound mp. 236.8–238.8° C.; IR (KBr) 3433, 2930, 2866, 1669, 1457, 1402, 1234, 1058, 1035 cm$^{-1}$; $^1$H NMR (CDCl$_3$) δ 6.46 (S, 1H, 1-H), 5.9 (S, 1H, 2-OH), 3.75 (D, 1H, 28H), 3.52 (S, 1H, 19-H), 3.52 (S, 1H, 28H), 0.78, 0.91, 0.99, 1.01, 1.09, 1.13, 1.19 (all S, 7×3, 23-, 24-, 25-, 26-, 27-, 29-, 30-Me), 1.05–1.78 (complex CH—, CH$_2$, 25H); $^{13}$C NMR (CDCl$_3$) δ 201.43, 144.202, 129.29, 88.16, 71.523, 54.49, 46.99, 43.3, 41.75, 41.312, 38.97, 36.98, 36.56, 34.53, 33.83, 32.97, 29.1, 27.41, 26.6, 26.52, 24.86, 21.89, 21.51, 20.87, 18.96, 16.5, 13.64; MS(EI) 454, 383, 327, 281, 245, 215, 207, 191, 177, 151, 137, 136, 123, 109, 95, 81, 69, 55.

EXAMPLE 8

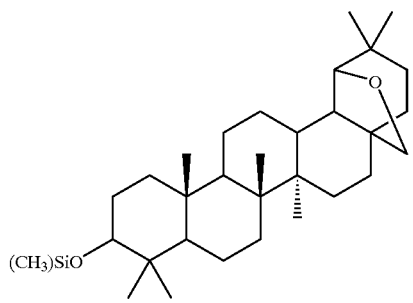

Allobetulin-3-Trimethylsilane.

Triethylamine (5 ml) and trimethylsilylchloride (2.45 g, 22.6 mmol) were added to allobetulin (1 g, 2.259 mmol) in 20 ml of dichloromethane at 20–25° C. After 10 hours stirring, the mixture was poured into 100 ml of cracked ice and the organic layer was separated. The aqueous layer was extracted with dichloromethane (3×10 ml), and the combined organic extracts were washed with water (3×20ml), 5% HCl (2×30 ml) and water (2×20 ml), and dried over $Na_2SO_4$ (anh.). Evaporation of the solvent gave 1.14 g of light-yellow crystals, which after chromatography on silica gel with hexane gave white crystals. Additional chromatography on silica gel with hexane gives white crystals mp. 211.8–214.9° C.; IR (KBr) 2948, 2868, 1782, 1451, 1387, 1249, 1099, 1066, 892, 840 cm$^{-1}$; $^1$H NMR (CDCl$_3$) δ 3.738(D, 1H, 28H, J1=7.81 Hz), 3.49(S, 1H, 19H), 3.403(D, 1H, 28H, J1=7.81 Hz), 3.146(DD, 1H, 3H, J1=10.5, J2=10.5), 0.933, 0.895, 0.879, 0.832, 0.808, 0.736, 0.697 (all S, 7×3H, 23-, 24-, 25-, 26-, 27-, 29-, 30-Me), 1.1–1.92 (complex CH—, CH$_2$—, 24H), 0.065(S, 3×3H, 3 Me$_{si}$); $^{13}$C NMR (CDCl$_3$) δ 88.225, 79.91, 71.574, 55.9, 51.448, 47.149, 41.778, 40.999, 40.918, 39.527, 39.301, 37.508, 37.071, 36.575, 34.448, 34.309, 33.027, 29.143, 28.13, 26.811, 26.592, 24.887, 21.309, 18.796, 16.894, 16.187, 16.012, 13.819, 0.826; MS (EI) 514, 499, 483, 457, 443, 424, 409, 385, 355, 343, 323, 279, 247, 203, 189, 176, 165, 148, 135, 129, 122, 107, 95, 82, 73, 55, 42;

EXAMPLE 9

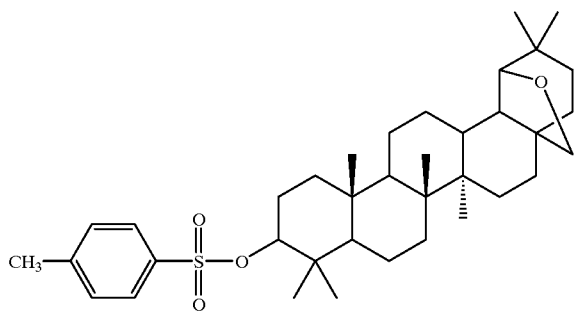

Allobetulin Tosylate

Betulin (3 g) and p-toluenesulfonyl chloride (2.52 g) were placed in dry pyridine (70 ml) at 3–5° C. After 72 hours at 3–5° C. the solution was poured into 100 ml of cracked ice and the resulting precipitate was washed with water (2×50 ml), 1% HCl (50 ml) and water (2×50 ml) and dried in an oven. Chromatography on a silica column (Ether:Hexane=25:75) gave 2.96 g of allobetulin tosylate as white crystals mp. 180–182.6° C. (dec); IR (KBr) 2944, 2864, 1489, 1451, 1363, 1337, 1174, 1098, 1036, 925, 905, 875, 812, 685, 560 cm$^{-1}$; $^1$H NMR (CDCl$_3$) δ 7.8(D, 2H, benz-Tos), 7.37(D, 2H, benz-Tos), 4.22(DD, 1H, 3H), 3.76(D, 1H, 28H, J=11 Hz), 3.52(S, 1H, 19H), 3.39(D, 1H, 28H, J=11 Hz), 2.44(S, 3H, Tos-Me), 0.8, 0.8, 0.83, 0.92, 0.93, 0.96, 0.99, (all S, 7×3H, 23-, 24-, 25-, 26-, 27-, 29-, 30-Me), 0.6–1.86 (complex CH—, CH$_2$—, 25H); $^{13}$C NMR (CDCl$_3$) δ 144.46, 135.08, 129.88, 129.88, 127.83, 127.83, 91.18, 88.10, 71.42, 55.93, 51.1, 46.98, 41.65, 40.9, 40.76, 38.95, 38.84, 37.16, 36.92, 36.46, 34.29, 33.97, 32.90, 29.03, 27.98, 26.59, 26.43, 25.04, 24.76, 21.86, 21.23, 18.47, 16.67, 16.43, 15.87, 13.69.

EXAMPLE 10

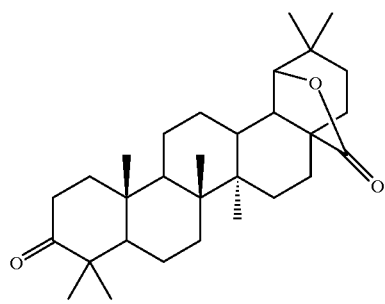

Allobetulon Lactone

Dry DMSO (22 mmol, 1.76 g) in 25 ml of dry dichloromethane was added drop wise over 3–5 minutes to a solution of COCl$_2$ (11 mmol, 1.397 g) in 25 ml of dry dichloromethane at −50–60° C. (I-Pr alcohol—dry ice bath). After 5 minutes, crystals of allobetulin-lactone (10 mmol, 4.56 g) were added and the solution was allowed to stand for 30 minutes. Triethylamine (25-mmol, 2.53 g) was added and the temperature was allowed to increase to 10° C. The solution was poured into 100 ml of cracked ice, extracted with dichloromethane (3×20 ml) and washed with water (5×10 ml), 5% HCl (2×10 ml), and H$_2$O(2×10 ml). The organics were dried over sodium sulfate and evaporated to give 4.5 g of crude compound. Column chromatography (hexane: ether=80:20) gives 4.15 g of white crystals mp. 333.7–335.9° C.(dec.); IR (KBr) 2942, 2866, 1760, 1709, 1448, 1385, 1153, 1118, 967, 924 cm$^{-1}$; $^1$H NMR (CDCl$_3$) δ 3.947(s, 1H, 19H), 2.48(M, 2H, 2H), 1.075, 1.031, 1.031, 0.961, 0.994, 0.994, 0.885(all S, 7×3H, 23-, 24-, 25-, 26-, 27-, 29-, 30-Me), 1.1–2.0 (complex CH—, CH$_2$—, 23H); $^{13}$C NMR (CDCl$_3$) δ 218.12, 180.003, 86.206, 55.266, 50.843, 47.571, 46.952, 46.369, 40.78, 40.27, 40.124, 37.26, 36.422, 34.309, 33.843, 33.289, 32.611, 32.218, 29.034, 28.152, 27.022, 26.755, 25.805, 24.232, 21.688, 21.244, 19.808, 16.646, 15.604, 13.862; MS (EI) 454, 439, 437, 411, 369, 368, 356, 327, 309, 262, 248, 235, 207, 190, 175, 164, 146, 134, 121, 107, 78, 69, 55, 42.

EXAMPLE 11

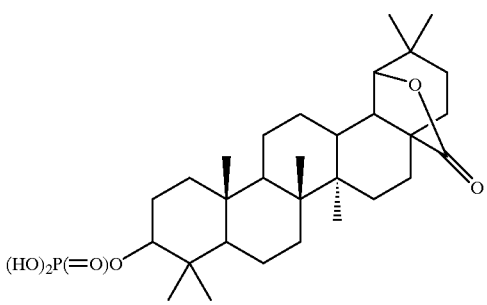

Allobetulinlacton-3-Phosphate

A solution of Allobetulin-3-phosphodichloride in 50 ml of dioxane and 1 ml of water was allowed to reflux for 18 hours. The solution was diluted with cold water (50 ml) and the resulting precipitate was collected by filtration, washed with water (3×30 ml), and dried in an oven (temperature not higher than 110° C.) to give 3.12 g of white crystalline compound mp. 226.7–230.1° C. (dec); IR (KBr) 3414, 2945, 2868, 1760, 167, 1449, 1384, 1524, 1213, 1068, 1025, 967, 495 cm$^{-1}$; $^1$H NMR (CDCl$_3$/DMSO$_{d6}$=1:1) δ 5.64(S, 2H, (OH)$_2$) 3.94 (S, 1H, 19H), 3.81(M, 1H, 3-H), 1.001, 0.98, 0.98, 0.89, 0.89, 0.87, 0.78 (all S, 7×3H, 23-, 24-, 25-, 26-, 27-, 29-, 30-Me), 1.05–1.95(complex CH—, CH$_2$, 23H); $^{13}$C NMR(CDCl$_3$/DMSO$_{d6}$) δ 177.852, 84.195, 82.504, 53.984, 49.510, 44.897, 44.431, 38.995, 38.405, 38.405, 37.275, 37.181, 35.556, 34.608, 32.065, 30.928, 30.243, 27.38, 26.637, 26.345, 24.851, 24.057, 23.758, 22.381, 19.408, 16.712, 15.174, 14.817, 14.059, 12.296; $^{31}$p NMR (D$_3$PO$_4$85% in D$_2$O) δ-0.719.

EXAMPLE 12

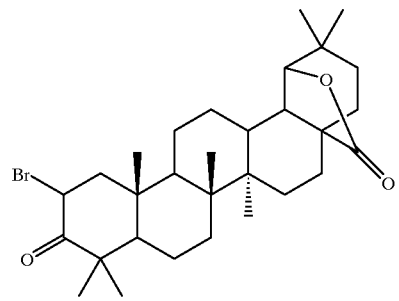

2-Br-Allobetulonlacton

Trifluoroacetic acid (99%, 10 ml) was added to Betulin (2 g) in 50 ml of CH$_2$Cl$_2$ at 0° C. Powdered NaBrO$_3$ (3.24 g) was added and the mixture was stirred for 16 hours at room temperature. The solution was poured into 100 ml of cracked ice and the organics were separated. The aqueous phase was extracted with dichloromethane (3×10 ml) and the combined organics were washed with 10% aqueous NaHSO$_3$(2×30 ml) and water (2×20 ml), dried over Na$_2$SO$_4$(anh.), and evaporated to give 2.34 g of light-yellow crystals which was recrystallized from hexane-chloroform to yield white needles mp. 338.0–342.8° C. (dec.); IR (KBr) 2949, 2869, 1765, 1721, 1450, 1389, 1196, 1153, 1119, 1051, 969, 922, 759 cm$^{-1}$; $^1$H NMR (CDCl$_3$) δ 5.108(DD, 1H, 2H, J1=6.1 Hz, J2=6.34 Hz), 3.96(S, 1H, 19H), 2.692(DD, 1H, 2H, J1=6.34 Hz, J2=6.1 Hz), 1.211, 1.158, 1.112, 1.049, 0.979, 0.882, (all S 7×3H, 23-, 24-, 25-, 26-, 27-, 29-, 30-Me), 1.1–1.92 (complex CH—, CH$_2$—, 24H); $^{13}$C NMR (CDCl$_3$) δ 207.096, 179.923, 86.192, 56.979, 53.139, 52.607, 50.800, 49.503, 46.887, 46.318, 40.977, 40.365, 40.285, 36.226, 33.814, 33.515, 32.568, 32.167, 28.998, 28.094, 26.578, 26.513, 25.740, 24.203, 22.002, 21.456, 19.372, 16.573, 15.881, 13.834; MS (EI) 534, 488, 454, 437, 407, 368, 327, 309, 281, 260, 235, 203, 190, 175, 166, 149, 135, 119, 107, 95, 81, 69, 55, 41.

EXAMPLE 13

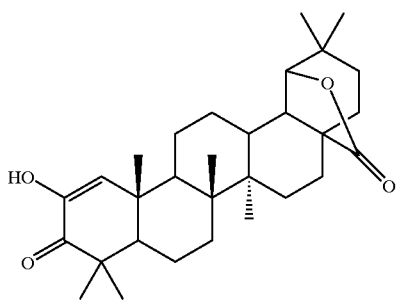

Allobetulonlacton 1-ene-2-ol

To a solution of Allobetulonlacton (1.0 g) in dry benzene-tert-butyl alcohol (1:1, 40 ml) was added a solution of potassium tert-butoxide (0.56 g) in tert-butyl alcohol (20 ml) and oxygen was bubbled into the stirred mixture for 3 hours. The mixture was acidified with 2.0 ml of glacial acetic acid and diluted with 30 cc dichloromethane. After washing with water (2×15 ml), 5% aqueous NaHCO$_3$ (2×30 ml) and water (30 ml), the extract was dried over Na$_2$SO$_4$ and evaporated to give crystals (m=0.983 g, 98%), which after chromatography on silica gel (hexane: ether=40:60) yield white crystalline compound mp. 238.8–243.6° C. (dec); IR (KBr) 2451, 2944, 2864, 1764, 1663, 1642, 1450, 1405, 1384, 1234, 1055, 967 cm$^{-1}$; $^1$H NMR (CDCl$_3$) δ 6.47(S, 1H, 2-H), 6.07–5.85(1H, OH), 3.96(S, 1H, 19H), 1.207, 1.153, 1.109, 1.037, 0.98, 0.974, 0.877 (all S, 7×3H, 23-, 24-, 25-, 26-, 27-, 20-, 30Me), 1.05–1.91 (complex CH—, CH$_2$22H); $^{13}$C NMR (CDCl$_3$) δ 201.36, 180.025, 144.217, 128.966, 86.192, 54.501, 46.879, 46.631, 46.376, 44.292, 41.654, 40.525, 38.936, 36.393, 33.836, 33.632, 32.568, 32.174, 29.034, 28.006, 27.365, 26.571, 25.784, 24.232, 21.841, 21.397, 20.923, 18.868, 16.282, 13.768; MS (EI) 468, 454, 441, 425, 407, 369, 340, 313, 303, 269, 259, 234, 215, 207, 189, 176, 165, 153, 151, 135, 128, 124, 108, 95, 78, 69, 55, 43.

EXAMPLE 14

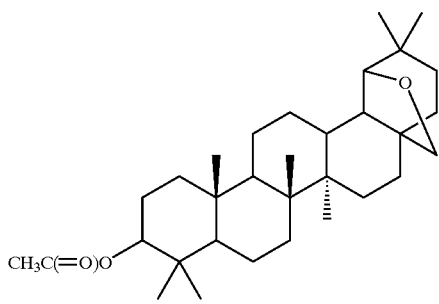

Allobetulin Acetate

Trifluoroacetic acid (99%, 10 ml) was added to Betulin-3-acetate (2 g) in 50 ml of dichloromethane at 0° C. After 30 minutes, the solution was poured into 100 ml of cracked ice and the organics were separated. The aqueous phase was extracted with dichloromethane (3× ml) and the combined organic extracts were washed with 5% NaHCO$_3$ (2×20 ml) and water (2×20 ml), dried over Na$_2$SO$_4$ (anh.), and evaporated to gives 1.98 g of Allobetulin acetate, which was recrystallized from hexane-dichloromethane to yield white needles mp. 282.2–283.4° C. [lit. 283–284° C.], IR (KBr) 2934.77, 2930.63, 2870.26, 1727.92, 1490.45, 1446.6, 1372.8, 1041.63, 999.14 cm$^{-1}$; $^1$H NMR (CDCl$_3$), δ 4.51 (DD, 1H, 3-H), 3.81 (D, J=10.3 Hz, 1H, 28-H), 3.53 (S, 1-H, 19-H), 3.49 (D, J=10.3 Hz, 1H, 28-H), 2.2 (S, 3H, Ac-Me), 0.74, 0.78, 0.79, 0.81, 0.85, 0.86, 1.10 (all S, 7×3H, 27-, 23-, 24-, 25-, 26-, 29-, 30- Me), 1.01–1.81 (complex CH—, CH$_2$, 25H,); $^{13}$C NMR (CDCl$_3$) δ 171.2, 88.2, 88.1, 71.49, 55.8, 51.3, 47.1, 41.7, 41.0, 41.0, 40.87, 38.9, 38.1, 37.4, 37.0, 36.5, 34.4, 34.1, 33.0, 29.1, 28.2, 26.7, 26.7, 26.6, 24.8, 24.06, 21.6, 21.3, 18.4, 16.8, 16.01, 15.8, 13.8; MS (EI) 484, 424, 413, 411, 381, 355, 342, 273, 257, 245, 231, 220, 203, 189, 177, 162, 149, 135.

EXAMPLE 15

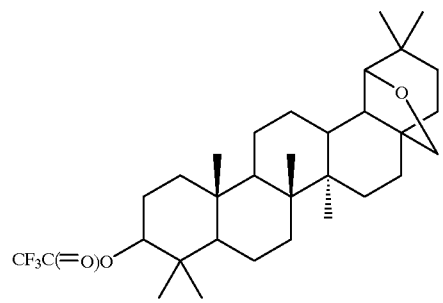

Allobetulin Trifluoroacetate

Trifluoroacetic acid (99%, 10 ml) was added to Betulin-3-acetate (2 g) in 50 ml of dichloromethane at 0° C. After 1 hour, trifluoroacetic anhydride (1 g) was added and the solution was allowed to stir for an additional 30 minutes. Evaporation of the solvent gives 2.39 g of Allobetulin trifluoroacetate, which was recrystallized from hexane-dichloromethane to yield white needles mp. 265.5–266.8° C. (dec); IR (KBr) 2947, 2853, 1769, 1452, 1468, 1236, 1179, 1034, 961, cm$^{-1}$; $^1$H NMR (CDCl$_3$), δ 4.72 (DD, 1H, 3-H), 3.05 (D, 1H, 28H, J=8 Hz), 3.56 (S, 1H, 19H), 3.47 (D, 1H, 28H, J=8 Hz), 0.68, 0.929, 0.929, 0.95, 0.95, 0.961, 1.015 (all S 7×3H, 23-, 24-, 25-, 26-, 27-, 29-, 30-Me), 1.05–1.79 (complex CH—, CH$_2$25H); $^{13}$C NMR (CDCl$_3$) 157.654 (Q, CF$_3$—CO—), 88.217, 86.541, 71.545, 55.733, 51.273, 47.112, 41.764, 41.035, 40.926, 38.725, 38.375, 37.443, 37.035, 36.568, 34.419, 34.076, 33.005, 30.032, 29.106, 28.057, 26.724, 26.549, 24.844, 23.554, 21.346, 18.373, 16.821, 16.551, 15.997, 13.782; $^{19}$F(CFCl$_3$δ75.8 S; MS (EI) 538, 509, 467, 424, 410, 356, 316, 303, 245, 220, 203, 191, 189, 177, 149, 135, 121, 107, 95, 81, 69.

EXAMPLE 16

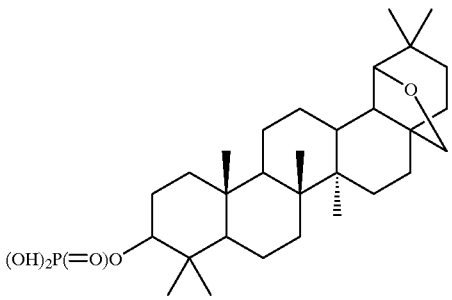

Allobetulin Phosphate

A solution of allobetulin-3-phosphodichloride 4 g in 50 ml of dioxane and 1 ml of water was refluxed for 18 hours. The mixture was diluted with cold water (50 ml) and the resulting white precipitate was filtered, washed with water (3×30 ml), and dried in an oven (temperature not higher than 110° C.) to give 3.12 g of white crystalline compound mp. 167.0–168.1° C. (dec); IR (KBr) 3469, 2947, 2868, 1775, 1467, 1388, 1221, 1169, 1022, 884, 585, 505, 481 cm$^{-1}$, $^{31}$P; $^{31}$P NMR (D$_3$PO$_4$85% in D$_2$O) δ −0.684.

EXAMPLE 17

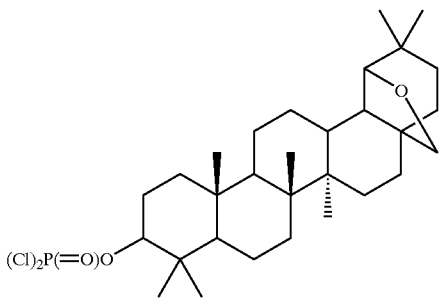

Allobetulin Phosphodichloride

In 50 mL round bottom 1-neck flask, dissolve 3 g of allobetulin in 25 mL of dry pyridine. Cool the solution down to −50–60° C. and add 4.6 mL of POCl$_3$. Stir the solution for 10 minutes and then add acetone in dropwise during 45 minutes. Stir at −50–60° C. for 1 hour and pour the reaction mixture into 200 mL of cracked ice. Filtrate white precipitate and wash it with cold water. Drying in oven (temperature not higher than 100° C.) gives 2.96 g of white crystalline compound m.p. 147–149° C. (dec), IR (KBr) 2941, 2866, 1774, 1467, 1374, 1285, 1169, 1001, 898, 616, 584 cm$^{-1}$; $^1$H NMR (CDCl$_3$) δ 4.47 (M, 1H, 3-H), 3.78 (DD, 1H, 28H, J=10.3), 3.53 (S, 1H, 19H), 3.49 (DD, 1H, 28H, J=10.3 Hz), 1.039, 0.982, 0.934, 0.915, 0.896, 0.882, 0.801, (all S, 7×3H, 23-, 24-, 25-, 26-, 27-, 29-, 30-Me), 1.05–2.08 (complex CH—, CH$_2$—, 24H); $^{13}$C NMR (CDCl$_3$) δ 94.301, 88.196, 71.509, 55.776, 51.200, 47.061, 41.727, 40.999, 40.86, 39.527, 39.432, 38.98, 37.297, 36.991, 36.532, 34.368, 34.061, 32.954, 29.085, 28.407, 26.68, 26.498, 25.594, 24.829, 21.339, 18.599, 16.784, 16.311, 15.961, 13.760; $^{31}$P NMR (D$_3$PO$_4$85% in D$_2$O) δ 7.505.

EXAMPLE 18

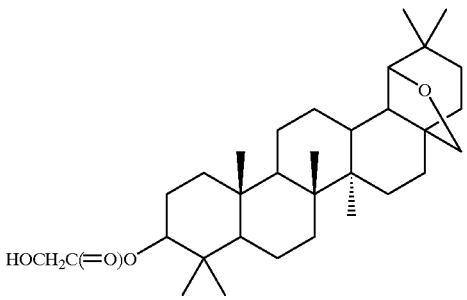

Allobetulin, 3-Glycolate

In 25-ml flask, stir diglycolic anhydride 0.39 g and 0.5 g Allobetulin in 15 ml CHCl$_3$. Then reflux for 24 hours. Add 10 ml saturated NaHCO$_3$, shake gently. Then separate the organic part, use the CHCl$_3$ (2×5 ml) wash and combine the organic parts. Use 3% HCl (10 ml) and water (2×10 ml) to wash it. Then use Na$_2$SO$_4$ (anhy.) to dry the organic part. Evaporate the solvent, get white granular 0.57 g. IR(KBr): 2964.07, 1753.33, 1223.67, 1110.16 cm$^{-1}$; $^1$H NMR (CDCl$_3$): δ 4.64 (DD, 1H, 3H), 4.32 (S, 4H, 33H$_2$, 32H$_2$), 3.66 (D, 1H, 28H, J=9 Hz), 3.54(S, 1H, 19H), 3.46 (D, 1H, 28H, J=9 Hz), 0.97, 0.926, 0.891, 0.866, 0.852, 0.828, 0.796 (all S, 7×3H, 27, 23, 24, 25, 26, 29, 30-Me), 1.1–1.9 (complex CH—, CH$_2$, 24H); $^{13}$C NMR (CDCl$_3$): δ 171.28, 88.342, 83.431, 71.597, 69.498, 55.872, 51.339, 47.164, 41.837, 41.094, 40.985, 38.886, 38.289, 37.509, 37.079, 36.627, 34.478, 34.157, 33.057, 29.166, 28.408, 26.775, 26.601, 24.917, 24.072, 21.391, 18.476, 16.916, 16.064, 13.87.

EXAMPLE 19

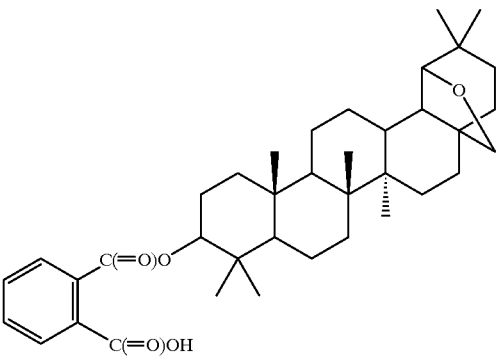

Allobetulin, 3-Phthalate

In 25-ml flask, stir phthalic anhydride 0.20 g and imidazole 0.38 g in 15 ml CH$_2$Cl$_2$, add the 0.5 g Allobetulin into the flask, and then reflux for 6 hours. Add 10 ml 3% HCl into the flask, dissolve the solid, separate the organic part, use the CH$_2$Cl$_2$ (3×5 ml) wash and combine the organic parts. Use warm water (2×15 ml) wash again. Use MgSO$_4$ (anhy.) to dry the organic part. Evaporate the solvent, get granular with little yellow color 0.44 g. m.p.: 252.3–253.9° C.; IR (KBr): 2948.90, 2868.36, 1724.74, 1660.31, 1458.97, 1289.84, 1136.82, 1072.39, 975.75 cm$^{-1}$; $^1$H NMR (CDCl$_3$): δ 7.95 (D, J=6.6 Hz, 1H, 33-H), 7.75 (D, J=6.9 Hz, 1H, 36-H), 7.62

(M, 2H, 34, 35-H), 4.82 (M, 1H, 3-H), 3.85 (D, 1H, 28-H), 3.66 (S, 1H, 19-H), 3.51 (D, J=7.5 Hz, 1H, 28-H), 2.0–0.8 (complex, CH—, CH$_2$—, 45H); $^{13}$C NMR (CDCl$_3$): 166.47, 163.55, 129.22, 127.32, 126.21, 125.98, 125.44, 124.28, 83.47, 78.42, 66.75, 51.23, 46.53, 42.31, 37.02, 36.25, 36.16, 34.15, 33.60, 32.72, 32.24, 31.77, 29.66, 29.37, 28.24, 24.31, 23.57, 21.96, 21.77, 20.08, 18.62, 16.60, 13.67, 12.19, 12.12, 11.26, 9.06.

EXAMPLE 20

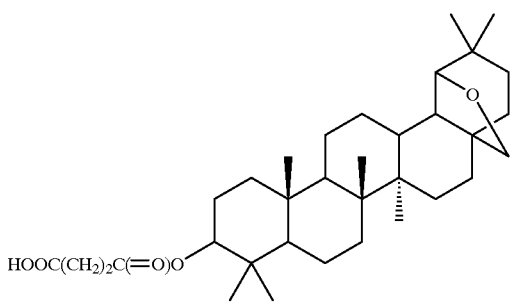

Allobetulin, 3-Succinate

In 25-ml flask, stir succinic anhydride 0.23 g and imidazole 0.46 g in 15 ml CH$_2$Cl$_2$, add the 0.5 g Allobetulin into the flask, and then reflux for 24 hours. Add 10 ml 3% HCl to dissolve the solid, then separate the organic part, use the CH$_2$Cl$_2$ (2×5 ml) wash and combine the organic parts. Use water (2×10 ml) to wash the organic part. Use P$_2$O$_5$ to dry the organic part. Evaporate the solvent, get white granular 0.48 g. m.p.: (decomp.) 258.1–259.5° C.; IR(KBr): 2940.85, 2868.36, 1732.79, 1450.91, 1386.49, 1225.41, 1169.04 cm$^{-1}$; $^1$H NMR (CDCl$_3$): δ 4.52 (M, 1H, 3-H), 3.78 (D, J=7.5 Hz, 1H, 28-H), 3.55 (S, 1H, 19-H), 3.45 (D, J=7.5 Hz, 1H, 28-H), 2.65 (M, 4H, 32, 33—CH$_2$), 0.76, 0.78, 0.84, 0.86, 0.90, 0.92, 1.0 (all S, 7×3H, 27, 23, 24, 25, 26, 29, 30-Me), 1.1–1.9 (complex CH—, CH$_2$, 24H); $^{13}$C NMR (CDCl$_3$): 172.78, 167.44, 83.50, 77.00, 66.73, 51.10, 46.50, 42.31, 36.99, 36.14, 34.08, 33.38, 32.67, 32.23, 31.77, 29.62, 29.35, 28.21, 24.93, 24.56, 24.32, 23.41, 21.94, 21.76, 20.08, 19.14, 16.54, 13.65, 12.07, 11.22, 9.04.

EXAMPLE 21

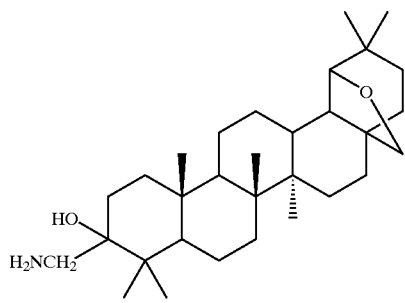

Allobetulin-3-Methylamine-3-ol

In 25 ml round bottom flask boil the mixture of Allobetulin (0.86 g, 1.955 mmol), ZnI$_2$ (20 mg, 0.063 mmol) and tert-Butildimethylsilylcyanide (0.420 g, 3.78 mmol) in 15 ml of Toluene for 24 hours. Add the above-mentioned mixture to a suspension of LiAlH$_4$ (0.37 g, 10 mmol) in 30 ml of THF in dropwise and boil for 2 hours. After those add 0.5 ml of concentrated KOH, dilute with 30 ml of THF and filtrate with diatomated earth. Dry over sodium sulfate and bubble HCl$_{gas}$ through the THF solution and filtrate the white precipitate (0.98 g). Dissolve the crystals in 50 ml of chloroform and wash with 1% NaHCO$_3$ until neutral reaction of universal paper indicator, separate organic part and dry over sodium sulfate. Evaporation of solvent gives 0.89 g (96% yield) of white crystalline compound m.p. 222.0–224.3° C., IR (KBr) 3414, 2939, 2868, 1617, 1461, 1384, 1036 cm$^{-1}$; $^1$H NMR (CDCl$_3$) δ 3.67 (D, 1H, 28H, J=7.5 Hz), 3.521 (S, 1H, 19H), 3.437 (D, 1H, 28H, J=7.5 Hz), 2.95 (D, 1H, 31H, J=13.2 Hz), 2.757 (D, 1H, 31H, J=13.2 Hz), 2.523 (S, 3H, OH+NH$_2$), 0.972, 0.926, 0.911, 0.904, 0.894, 0.824, 0.798, all S, 7×3H, 23-, 24-, 25-, 26-, 27-,29-, 30-Me), 1.01–1.79 (complex CH—, CH$_2$—, 24H); $^{13}$C NMR (CDCl$_3$) δ 88.13, 75.174, 71.428, 62.517, 53.554, 51.703, 47.018, 43.265, 41.669, 40.911, 40.882, 40.882, 37.683, 37.596, 36.933, 36.459, 34.309, 32.903, 30.265, 29.048, 27.416, 26.643, 26.454, 24.771, 24.166, 21.171, 19.947, 18.905, 17.076, 15.961, 13.811.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A therapeutic method for treating a human afflicted with herpesvirus infection comprising administering to said human, an effective anti-viral amount of a compound of formula

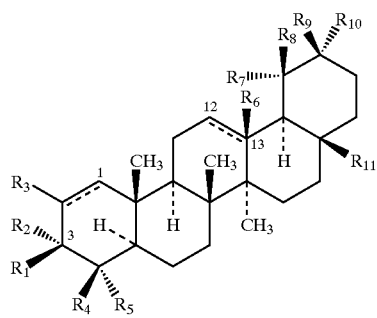

(I)

wherein
one of $R_1$ and $R_2$ is —O—Y and the other is hydrogen or (C$_1$–C$_6$)alkyl optionally substituted by hydroxy, (C$_1$–C$_6$)alkoxy, halo, halo(C$_1$–C$_6$)alkoxy or NR$_j$R$_k$ wherein R$_j$ and R$_k$ are independently H, (C$_1$–C$_6$)alkyl or (C$_1$–C$_6$)alkonyl; or $R_1$ and $R_2$ together are oxo (=O);

$R_3$ is hydrogen, halo, carboxy, mercapto, (C$_1$–C$_6$)alkyl, (C$_3$–C$_8$)cycloalkyl, or —O—Y;

$R_4$ and $R_5$ are each independently hydrogen, (C$_1$–C$_6$) alkyl, or hydroxy(C$_1$–C$_6$)alkyl;

$R_6$ is hydrogen or is absent when the adjacent—is a bond;

$R_7$ is hydrogen or (C$_1$–C$_6$)alkyl;

$R_8$ is hydrogen, (C$_1$–C$_6$)alkyl, or hydroxy(C$_1$–C$_6$)alkyl and $R_{11}$ is hydrogen, (C$_1$–C$_6$)alkyl, carboxy, or hydroxy(C$_1$–C$_6$)alkyl; or $R_8$ and $R_{11}$ together are —O—C(=X)—;

$R_9$ and $R_{10}$, are each independently hydrogen or (C$_1$–C$_6$) alkyl;

each of the bonds represented by --- is independently absent or is present;

X is two hydrogens, oxo (=O) or thioxo (=S);

each Y is independently H, aryl, P(O)(Cl)$_2$, (C$_3$–C$_8$) cycloalkyl, adamantyl, —SO$_2$R$_a$ O=P(R$_b$)$_2$, O=P (R$_c$)$_2$ OP(O)(R$_d$)—, Si(R$_e$)$_3$, tetrahydropyran-2-yl, an amino acid, a peptide, a glycoside, or a 1 to 10 membered branched or unbranched carbon chain optionally comprising 1, 2, or 3 heteroatoms selected from non-peroxide oxy, thio, and —N(R$_f$)—; wherein said chain may optionally be substituted on carbon with 1, 2, 3, or 4 oxo (=O), hydroxy, carboxy, halo, mercapto, nitro, —N(R$_g$)(R$_h$), (C$_3$–C$_8$)cycloalkyl, (C$_3$–C$_8$)cycloalkyloxy, aryl, aryloxy, adamantyl, adamantyloxy, hydroxyamino, trifluoroacetylamino, a glycoside, an amino acid, or a peptide; and wherein said chain may optionally be saturated or unsaturated R$_a$ is (C$_1$–C$_6$)alkyl or aryl;

R$_b$, R$_c$, and R$_d$ are each independently hydroxy, (C$_1$–C$_6$) alkoxy, hydroxy(C$_2$–C$_6$)alkoxy, adamantyloxy, adamantyl(C$_1$–C$_6$)alkoxy, norbornyloxy, 1,1-di(hydroxymethyl)-2-hydroxyethoxy, carboxy(C$_1$–C$_6$) alkoxy, 2,3-epoxypropyloxy, benzyloxy, (C$_3$–C$_8$) cycloalkyloxy, NR$_x$R$_y$, or aryloxy;

R$_e$ is H, aryl or (C$_1$–C$_6$)alkyl;

R$_f$ is hydrogen, (C$_1$–C$_6$)alkyl, (C$_1$–C$_6$)alkanoyl, phenyl or benzyl;

R$_g$ and R$_h$ are each independently selected from the group consisting of hydrogen, (C$_1$–C$_6$)alkyl, hydroxy(C$_1$–C$_6$) alkyl, adamantyl, adamantyl(C$_1$–C$_6$)alkyl, amino (C$_1$–C$_6$)alkyl, aminosulfonyl, (C$_1$–C$_6$)alkanoyl, aryl and benzyl; or R$_b$ and R$_c$ together with the nitrogen to which they are attached form a pyrrolidino, piperidino, or morpholino radical; and R$_x$ and R$_y$ are each independently hydrogen, (C$_1$–C$_6$) alkyl, (C$_1$–C$_6$)alkanoyl, aryl or benzyl;

wherein each aryl of Y, R$_a$–R$_d$, R$_g$–R$_h$, R$_x$, and R$_y$ may optionally be substituted by 1, 2, or 3 aminosulfonyl, carboxy, NR$_i$R$_j$, (C$_1$–C$_6$)alkyl, (C$_1$–C$_6$)alkoxy, hydroxy, halo, nitro, cyano, mercapto, carboxy, hydroxy(C$_1$–C$_6$)alkyl, halo(C$_1$–C$_6$)alkyl, trifluoromethoxy, (C$_1$–C$_6$)alkanoyl, (C$_1$–C$_6$) alkoxycarbonyl, (C$_1$–C$_6$)alkylthio, or (C$_1$–C$_6$) alkanoyloxy; wherein R$_i$ and R$_j$ are each independently hydrogen, (C$_1$–C$_6$)alkyl, (C$_1$–C$_6$)alkanoyl, phenyl, or benzyl;

or a pharmaceutically acceptable salt thereof; provided the compound is not ursolic acid-3-one and 2,3-dihydroxyurs-12-en-28-oil acid.

2. The method of claim 1 wherein R$_1$ is —O—Y.

3. The method of claim 1 wherein R$_1$ and R$_2$ together are oxo (=O).

4. The method of claim 1 wherein R$_3$ is hydrogen.

5. The method of claim 1 wherein R$_3$ is hydroxy, halo, carboxy, mercapto, (C$_1$–C$_6$)alkyl, (C$_1$–C$_6$)alkoxy, (C$_3$–C$_8$) cycloalkyl, or (C$_3$–C$_8$)cycloalkyloxy.

6. The method of claim 1 wherein R$_3$ is —O—Y.

7. The method of claim 1 wherein R$_4$ is methyl or hydroxymethyl.

8. The method of claim 1 wherein R$_5$ is methyl or hydroxymethyl.

9. The method of claim 1 wherein R$_4$ and R$_5$ are each methyl.

10. The method of claim 1 wherein R$_4$ is hydroxymethyl and R$_5$ is methyl.

11. The method of claim 1 wherein R$_6$ is hydrogen.

12. The method of claim 1 wherein R$_6$ is absent and the adjacent—is present.

13. The method of claim 1 wherein R$_7$ is hydrogen or methyl.

14. The method of claim 1 wherein R$_8$ is hydrogen or methyl.

15. The method of claim 1 wherein R$_9$ is hydrogen or methyl.

16. The method of claim 1 wherein R$_{10}$ is hydrogen or methyl.

17. The method of claim 1 wherein R$_7$ is hydrogen, R$_8$ is methyl, R$_9$ is hydrogen and R$_{10}$ is methyl.

18. The method of claim 1 wherein R$_7$ is hydrogen, R$_8$ is hydrogen, R$_9$ is methyl and R$_{10}$ is methyl.

19. The method of claim 1 wherein R$_8$ and R$_{11}$ together are —O—C(=X)—.

20. The method of claim 1 wherein R$_{11}$ is methyl.

21. The method of claim 1 wherein R$_{11}$ is carboxy.

22. The method of claim 1 wherein X is two hydrogens or is oxo.

23. The method of claim 1 wherein the bond at positions 1 and 2 represented by --- is present.

24. The method of claim 1 wherein the bond at positions 1 and 2 represented by --- is absent.

25. The method of claim 1 wherein the bond at positions 12 and 13 represented by --- is present.

26. The method of claim 1 wherein the bond at positions 12 and 13 represented by --- is absent.

27. The method of claim 1 wherein the compound of formula (I) is a compound of formula (II):

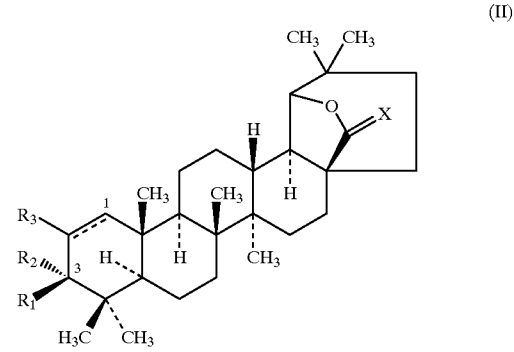

(II)

or a pharmaceutically acceptable salt thereof.

28. The method of claim 1 wherein the compound is a compound of formula (III):

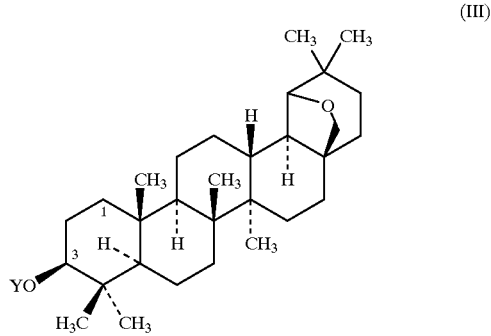

(III)

or a pharmaceutically acceptable salt thereof.

29. The method of claim 1 wherein Y is H.

30. The method of claim 1 wherein Y is O=P($R_b$)$_2$, or O=P($R_c$)$_2$OP(O)($R_d$)—.

31. The method of claim 1 wherein Y is —SO$_2$R$_a$, Si(R$_e$)$_3$, or tetrahydropyran-2-yl.

32. The method of claim 1 wherein Y is an amino acid, a peptide, or a glycoside.

33. The method of claim 1 wherein Y is a 1 to 10 membered branched or unbranched carbon chain optionally comprising 1, 2, or 3 heteroatoms selected from non-peroxide oxy, thio, and —N(R$_f$)—; wherein said chain may optionally be substituted on carbon with 1, 2, 3, or 4 oxo (=O), hydroxy, carboxy, halo, mercapto, nitro, —N(R$_g$)(R$_h$), (C$_3$–C$_8$)cycloalkyl, (C$_3$–C$_8$)cycloalkyloxy, aryl, aryloxy, adamantyl, adamantyloxy, hydroxyamino, trifluoroacetylamino, a glycoside, an amino acid, or a peptide; and wherein said chain may optionally be saturated or unsaturated.

34. The method of claim 1 wherein Y is (C$_1$–C$_{10}$)alkyl, (C$_2$–C$_{10}$)alkenyl, (C$_2$–C$_{10}$)alkynyl, or (C$_1$–C$_{10}$)alkanoyl, wherein any (C$_1$–C$_{10}$)alkyl, (C$_2$–C$_{10}$)alkenyl, (C$_2$–C$_{10}$)alkynyl, or (C$_1$–C$_{10}$)alkanoyl, is optionally substituted with hydroxy, carboxy, mercapto, —N(R$_g$)(R$_h$), (C$_3$–C$_8$) cycloalkyl, aryl, aryloxy, adamantyl, a glycoside, an amino acid, or a peptide.

35. The method of claim 1 wherein Y is (C$_1$–C$_{10}$)alkyl or (C$_1$–C$_{10}$)alkanoyl.

36. The method of claim 1 wherein Y is aryl, (C$_3$–C$_8$) cycloalkyl, or adamantyl.

37. The method of claim 1 wherein Y is H, —C(=O)C(=O)R$_k$, —C(=O)R$_m$, —SO$_2$R$_n$ O=P(R$_o$)$_2$, O=P(R$_p$)$_2$OP(O)(R$_q$)—, (C$_1$–C$_6$)alkanoyl, Si(R)$_3$, (C=O)N(R)$_2$, benzyl, benzoyl, tetrahydropyran-2-yl, 1-[(C$_1$–C$_4$)alkoxy](C$_1$–C$_4$)alkyl, an amino acid, a peptide, or a glycoside; wherein each R is H, phenyl or (C$_1$–C$_6$)alkyl;

R$_k$ is hydroxy, (C$_1$–C$_6$)alkoxy, aryloxy, aryl(C$_1$–C$_6$) alkoxy, (C$_3$–C$_8$)cycloalkyloxy, hydroxy(C$_2$–C$_6$)alkoxy, adamantyloxy, NRA, an amino acid, a peptide, hydroxyamino, amino(C$_1$–C$_6$)alkyl or a glycoside;

R$_m$ is aryl, carboxy(C$_1$–C$_6$)alkyl, aminocarbonyl(C$_1$–C$_6$) alkyl, trifluoroacetylamino(C$_1$–C$_6$)alkyl, amino (C$_1$–C$_6$)alkyl, vinyl, adamantyl, adamantyl(C$_1$–C$_6$) alkyl;

R$_n$ is (C$_1$–C$_6$)alkyl or aryl;

R$_o$, R$_p$, and R$_q$ are each independently hydroxy, (C$_1$–C$_6$) alkoxy, hydroxy(C$_2$–C$_6$)alkoxy, adamantyloxy, adamantyl(C$_1$–C$_6$)alkoxy, norbornyloxy, 1,1-di (hydroxymethyl)-2-hydroxyethoxy, carboxy(C$_1$–C$_6$) alkoxy, 2,3-epoxypropyloxy, benzyloxy, (C$_3$–C$_8$) cycloalkyloxy, NR$_v$R$_w$, or aryloxy;

R$_r$ and R$_s$ are each independently hydrogen, (C$_1$–C$_6$) alkyl, hydroxy(C$_1$–C$_6$)alkyl, adamantyl, adamantyl (C$_1$–C$_6$)alkyl, amino(C$_1$–C$_6$)alkyl, aminosulfonyl, (C$_1$–C$_6$)alkanoyl, or aryl; or R$_r$ and R$_s$ together with the nitrogen to which they are attached are pyrrolidino, piperidino, or morpholino; and R$_v$ and R$_w$ are each independently hydrogen, (C$_1$–C$_6$) alkyl, (C$_1$–C$_6$)alkanoyl, aryl or benzyl;

wherein each aryl of R$_k$, R$_m$, —R$_s$, R$_v$, and R$_w$ may optionally be substituted by 1,2, or 3 aminosulfonyl, carboxy, NR$_t$R$_u$, (C$_1$–C$_6$)alkyl, (C$_1$–C$_6$)alkoxy, hydroxy, halo, nitro, cyano, mercapto, carboxy, hydroxy(C$_1$–C$_6$)alkyl, halo(C$_1$–C$_6$)alkyl, trifluoromethoxy, (C$_1$–C$_6$)alkanoyl, (C$_1$–C$_6$) alkoxycarbonyl, (C$_1$–C$_6$)alkylthio, and (C$_1$–C$_6$) alkanoyloxy; and wherein R$_t$ and R$_u$ are each independently hydrogen, (C$_1$–C$_6$)alkyl, (C$_1$–C$_6$)alkanoyl, phenyl, or benzyl.

38. The method of claim 1 wherein Y is H, —C(=O)C(=O)R$_k$, —C(=O)R$_m$, —SO$_2$R$_n$ (C$_1$–C$_6$)alkanoyl, (C=O)N(R)$_2$, benzyl, benzoyl, an amino acid, a peptide, or a glycoside.

39. The method of claim 37 wherein Y is —C(=O)C(=O)R$_k$, —C(=O)R$_m$, (C$_1$–C$_6$)alkanoyl, (C=O)N(R)$_2$, benzyl, or benzoyl.

40. The method of claim 1 wherein Y is O=P(OH)$_2$ or O=P(OH)$_2$OP(O)(OH)—.

41. The method of claim 37 wherein Y is —SO$_2$R$_n$ (C$_1$–C$_6$)alkanoyl, Si(R)$_3$, benzyl, benzoyl, tetrahydropyran-2-yl, or 1-[(C$_1$–C$_4$)alkoxy](C$_1$–C$_4$)alkyl.

42. The method of claim 1 wherein the herpesvirus is HSV-1.

43. The method of claim 1 wherein the herpesvirus is HSV-2.

44. The method of claim 1 wherein the compound is allobetulin or uvaol, or a pharmaceutically acceptable salt thereof.

* * * * *

UNITED STATES PATENT AND TRADEMARK OFFICE
CERTIFICATE OF CORRECTION

PATENT NO. : 6,369,101 B1
DATED : April 9, 2002
INVENTOR(S) : Robert M. Carlson

It is certified that error appears in the above-identified patent and that said Letters Patent is hereby corrected as shown below:

Title page,
Item [56], FOREIGN PATENT DOCUMENTS, delete "12/1999" and insert
-- 12/1996 --, therefor.
Item [56], OTHER PUBLICATIONS,
9th reference, delete "Jääskläinen" and insert -- Jääskeläinen --, therefor.
9th reference, delete "Trära" and insert -- Trä --, therefor.
12th reference, delete "Mañz" and insert -- Máñez --, therefor.
17th reference, insert -- pp. -- before "71-81".
19th reference, delete "a" and insert -- as -- before "Potential".
20th reference, delete "Plant" and insert -- Planta --, therefor.
25th reference, delete "Phloiononolic" and insert -- Phloionolic --, therefor.
26th reference, insert -- ( -- before "Mar. 1, 1996".
29th reference, delete "Simples" and insert -- Simplex --, therefor.
32th reference, delete "Chapeter" and insert -- Chapter --, therefor.
Item [57], ABSTRACT, delete "," after "$R_1$-$R_{11}$".

Column 36,
Line 32, insert -- (I): -- after "formula".

Column 37,
Line 18, insert -- (e.g. containing one, two, three or more, double or triple bonds); -- after "unsaturated".
Line 51, delete "2,3-dibydroxyurs-12-en-28-oil acid" and insert
-- 2,3-dibydroxyurs-12-en-28-oic acid --, therefor.

Column 39,
Line 37, delete "NRA" and insert -- $NR_rR_s$ --, therefor.

Signed and Sealed this

Eighth Day of July, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,369,101 B1
APPLICATION NO. : 09/259626
DATED : April 9, 2002
INVENTOR(S) : Robert M. Carlson It is certified that error appears in the above-identified patent and that said Letters Patent is hereby corrected as shown below:

On the face page, in field (56) under "FOREIGN PATENT DOCUMENTS", delete "12/1999" and insert --12/1996--, therefor.

On the face page, in field (57) under "Abstract", delete " , " after "$R_1$-$R_{11}$".

In page 2, column 1, line 8, delete "Jaasklainen" and insert --Jaaskelainen--, therefor.

In page 2, column 1, line 9, delete "Trara" and insert --Tra--, therefor.

In page 2, column 1, line 16, delete "Manz" and insert --Manez--, therefor.

In page 2, column 1, line 35, insert --pp.-- before "71-81".

In page 2, column 1, line 40, delete "a" and insert --as-- before "Potential".

In page 2, column 1, line 45, delete "Plant" and insert --Planta--, therefor.

In page 2, column 1, line 61, delete "Phloionononolic" and insert --Phloionolic--, therefor.

In page 2, column 2, line 4, insert -- (-- before "Mar. 1, 1996".

In page 2, column 2, line 13, delete "Simples" and insert --Simplex--, therefor.

In page 2, column 2, line 25, delete "Chapeter" and insert --Chapter--, therefor.

In page 2, column 2, line 55, delete "544 571" and insert --544-571--, therefor.

In column 36, line 32, in claim 1, insert --(I):-- after "formula".

In column 37, line 18, in claim 1, insert --(e.g. containing one, two, three or more, double or triple bonds);-- after "unsaturated".

In column 37, line 51, in claim 1, delete "2,3-dibydroxyurs-12-en-28-oil acid" and insert --2,3-dibydroxyurs-12-en-28-oic acid --, therefor.

UNITED STATES PATENT AND TRADEMARK OFFICE
CERTIFICATE OF CORRECTION

| | |
|---|---|
| PATENT NO. | : 6,369,101 B1 |
| APPLICATION NO. | : 09/259626 |
| DATED | : April 9, 2002 |
| INVENTOR(S) | : Robert M. Carlson |

It is certified that error appears in the above-identified patent and that said Letters Patent is hereby corrected as shown below:

In column 39, line 37, in claim 37, delete "NRA" and insert --$NR_rR_s$--, therefor.

Signed and Sealed this

Twenty-ninth Day of May, 2007

JON W. DUDAS
*Director of the United States Patent and Trademark Office*

UNITED STATES PATENT AND TRADEMARK OFFICE
Certificate

Patent No. 6,369,101 B2　　　　　　　　　　　　　　　　　　　　　Patented: April 9, 2002

On petition requesting issuance of a certificate for correction of inventorship pursuant to 35 U.S.C. 256, it has been found that the above identified patent, through error and without any deceptive intent, improperly sets forth the inventorship.
　Accordingly, it is hereby certified that the correct inventorship of this patent is: Robert M. Carlson, Duluth, MN (US); and M. Reza-ul Karim, Duluth, MN (US).

Signed and Sealed this Eighteenth Day of September 2007.

WILLIAM R. DIXON, JR.
　　　　　　　　　　　　　　　　　　　　　　　　　　　*Special Program Examiner*
　　　　　　　　　　　　　　　　　　　　　　　　　　　Technology Center 1600